United States Patent [19]
Villhauer

[11] Patent Number: 6,011,155
[45] Date of Patent: Jan. 4, 2000

[54] N-(SUBSTITUTED GLYCYL)-2-CYANOPYRROLIDINES, PHARMACEUTICAL COMPOSITIONS CONTAINING THEM AND THEIR USE IN INHIBITING DIPEPTIDYL PEPTIDASE-IV

[75] Inventor: Edwin Bernard Villhauer, Morristown, N.J.

[73] Assignee: Novartis AG, Basle, Switzerland

[21] Appl. No.: 08/962,168

[22] Filed: Oct. 31, 1997

Related U.S. Application Data

[60] Provisional application No. 60/030,570, Nov. 7, 1996.

[51] Int. Cl.$^7$ .................. C07D 207/34; C07D 207/42; C07D 401/06; C07D 405/10; C07D 409/06
[52] U.S. Cl. .................. 544/333; 544/326; 544/330; 546/208; 546/276.4; 546/279.1; 548/530; 548/540
[58] Field of Search .................. 548/530, 540, 548/517; 546/276.4, 279.1, 208; 544/516, 330, 328, 333

[56] References Cited

U.S. PATENT DOCUMENTS

| | | | |
|---|---|---|---|
| 4,229,465 | 10/1980 | Ohkuma et al. | 424/27 X |
| 4,849,435 | 7/1989 | Wollweber, et al. | 514/343 |
| 4,923,883 | 5/1990 | Wollweber, et al. | 514/343 |
| 4,977,182 | 12/1990 | Wollweber, et al. | 514/423 |

FOREIGN PATENT DOCUMENTS

| | | |
|---|---|---|
| 0646454 | 11/1991 | Australia ............... 548/540 |
| 0339422 | 11/1989 | European Pat. Off. ........ 548/540 |
| 555 824 A1 | 8/1993 | European Pat. Off. . |
| 1581 09 | 12/1982 | Germany . |
| 296 075 A5 | 11/1991 | Germany . |
| WO90/12005 | 10/1990 | WIPO . |
| WO9116339 | 10/1991 | WIPO . |
| WO9308259 | 4/1993 | WIPO . |
| WO95/13069 | 5/1995 | WIPO . |
| WO9511689 | 5/1995 | WIPO . |
| WO95/15309 | 6/1995 | WIPO . |
| WO9529190 | 11/1995 | WIPO . |
| WO9529691 | 11/1995 | WIPO . |
| WO9534538 | 12/1995 | WIPO . |

OTHER PUBLICATIONS

Li et al, Archives of Biochemistry and Biophysics vol. 323, No. 1, pp. 148–154 (1995).
Li et al, Journal of Neurochemistry, vol. 66, pp. 2105–2112 (1996).
Yamada et al, Bulletin of the Chemical Society of Japan, vol. 50, No. 7, pp. 1827–1830 (1977).
Yamada et al., Bulletin of the Chemical Society of Japan, vol. 51, No. 3, pp. 878–883 (1978).
Chemical Abstracts 95: 302548. (1995).
Chemical Abstracts 84: 177689. (1984).
Chemical Abstracts 96: 116353 (1996).
Kaspari et al., Biochimica et Biophysica, vol. 1293, pp. 147–153. (1996).
Ashworth et al., Bioorganic and Medicinal Chemistry Letters, vol. 6, No. 10, pp. 1163–1166 (1996).
Coutts et al., J. Med. Chem., vol. 39, pp. 2087–2094 (1996).
Deacon et al., Diabetes, vol. 44, pp. 1126–1131 (Sep. '96).
Ashworth et al., Bioorganic and Medicinal Chemistry Letters, vol. 6, No. 22, pp. 2745–2748 (1996).
Augustyns et al., Eur. J. Med. Chem., vol. 32, pp. 301–309 (1997).

*Primary Examiner*—Floyd D. Higel
*Attorney, Agent, or Firm*—Joseph J. Borovian

[57] ABSTRACT

N-(N'-substituted glycyl)-2-cyanopyrrolidines of formula I

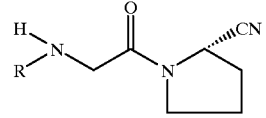

I

Compounds of formula I inhibit DPP-IV (dipeptidyl-peptidase-IV) activity. They are therefore indicated for use as pharmaceuticals in inhibiting DPP-IV and in the treatment of conditions mediated by DPP-IV, such as non-insulin-dependent diabetes mellitus, arthritis, obesity, osteoporosis and further conditions of impaired glucose tolerance.

11 Claims, No Drawings

N-(SUBSTITUTED GLYCYL)-2-CYANOPYRROLIDINES, PHARMACEUTICAL COMPOSITIONS CONTAINING THEM AND THEIR USE IN INHIBITING DIPEPTIDYL PEPTIDASE-IV

This application claims the benefit of Provisional Application number 60/030,570 filed on Nov. 7, 1996.

FIELD OF THE INVENTION

The present invention relates to the area of dipeptidyl peptidase-IV (DPP-IV) inhibition. DPP-IV is a serine protease which cleaves N-terminal dipeptides from a peptide chain containing, preferably, a proline residue in the penultimate position. Although the biological role of DPP-IV in mammalian systems has not been completely established, it is believed to play an important role in neuropeptide metabolism, T-cell activation, attachment of cancer cells to the endothelium and the entry of HIV into lymphoid cells.

More recently, it was discovered that DPP-IV is responsible for inactivating glucagon-like peptide-1 (GLP-1). More particularly, DPP-IV cleaves the amino-terminal His-Ala dipeptide of GLP-1, generating a GLP-1 receptor antagonist, and thereby shortens the physiological response to GLP-1. Since the half-life for DPP-IV cleavage is much shorter than the half-life for removal of GLP-1 from circulation, a significant increase in GLP-1 bioactivity (5- to 10-fold) is anticipated from DPP-IV inhibition. Since GLP-1 is a major stimulator of pancreatic insulin secretion and has direct beneficial effects on glucose disposal, DPP-IV inhibition appears to represent an attractive approach for treating non-insulin-dependent diabetes mellitus (NIDDM).

SUMMARY OF THE INVENTION

The present invention provides new DPP-IV inhibitors which are effective in treating conditions mediated by DPP-IV. More particularly, the present invention relates to certain N-(substituted glycyl)-2-cyanopyrrolidines which inhibit DPP-IV. In addition, the present invention provides pharmaceutical compositions useful in inhibiting DPP-IV comprising a therapeutically effective amount of a N-(substituted glycyl)-2-cyanopyrrolidine disclosed herein. Moreover, the present invention provides a method of inhibiting DPP-IV comprising administering to a mammal in need of such treatment a therapeutically effective amount of a N-(substituted glycyl)-2-cyanopyrrolidine.

DETAILED DESCRIPTION OF THE INVENTION

The instant invention relates to novel N-(substituted glycyl)-2-cyanopyrrolidines of formula I:

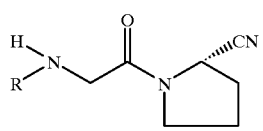

wherein R is:
a) $R_1R_{1a}N(CH_2)_m$- wherein
  $R_1$ is a pyridinyl or pyrimidinyl moiety optionally mono- or independently disubstituted with $(C_{1-4})$alkyl, $(C_{1-4})$alkoxy, halogen, trifluoromethyl, cyano or nitro; or phenyl optionally mono- or independently disubstituted with $(C_{1-4})$alkyl, $(C_{1-4})$alkoxy or halogen;
  $R_{1a}$ is hydrogen or $(C_{1-8})$alkyl; and
  m is 2 or 3;
b) $(C_{3-12})$cycloalkyl optionally monosubstituted in the 1-position with $(C_{1-3})$hydroxyalkyl;
c) $R_2(CH_2)_n$- wherein either
  $R_2$ is phenyl optionally mono- or independently di- or independently trisubstituted with $(C_{1-4})$alkyl, $(C_{1-4})$alkoxy, halogen or phenylthio optionally monosubstituted in the phenyl ring with hydroxymethyl; or is $(C_{1-8})$alkyl; a [3.1.1]bicyclic carbocyclic moiety optionally mono- or plurisubstituted with $(C_{1-8})$alkyl; a pyridinyl or naphthyl moiety optionally mono- or independently disubstituted with $(C_{1-4})$alkyl, $(C_{1-4})$alkoxy or halogen; cyclohexene; or adamantyl; and
  n is 1 to 3; or
  $R_2$ is phenoxy optionally mono- or independently disubstituted with $(C_{1-4})$alkyl, $(C_{1-4})$alkoxy or halogen; and
  n is 2 or 3;
d) $(R_3)_2CH(CH_2)_2$- wherein each $R_3$ independently is phenyl optionally mono- or independently disubstituted with $(C_{1-4})$alkyl, $(C_{1-4})$alkoxy or halogen;
e) $R_4(CH_2)_p$- wherein $R_4$ is 2-oxopyrrolidinyl or $(C_{2-4})$alkoxy and p is 2 to 4;
f) isopropyl optionally monosubstituted in 1-position with $(C_{1-3})$hydroxyalkyl;
g) $R_5$ wherein $R_5$ is: indanyl; a pyrrolidinyl or piperidinyl moiety optionally substituted with benzyl; a [2.2.1]- or [3.1.1]bicyclic carbocyclic moiety optionally mono- or plurisubstituted with $(C_{1-8})$alkyl; adamantyl; or $(C_{1-8})$alkyl optionally mono- or independently plurisubstituted with hydroxy, hydroxymethyl or phenyl optionally mono- or independently disubstituted with $(C_{1-4})$alkyl, $(C_{1-4})$alkoxy or halogen;
in free form or in acid addition salt form.

The compounds of formula I can exist in free form or in acid addition salt form. Salt forms may be recovered from the free form in known manner and vice-versa. Acid addition salts may e.g. be those of pharmaceutically acceptable organic or inorganic acids. Although the preferred acid addition salts are the hydrochlorides, salts of methanesulfonic, sulfuric, phosphoric, citric, lactic and acetic acid may also be utilized.

The compounds of the invention may exist in the form of optically active isomers or diastereoisomers and can be separated and recovered by conventional techniques, such as chromatography.

"Alkyl" and "alkoxy" are either straight or branched chain, of which examples of the latter are isopropyl and tert-butyl.

R preferably is a), b) or e) as defined above. $R_1$ preferably is a pyridinyl or pyrimidinyl moiety optionally substituted as defined above. $R_{1a}$ preferably is hydrogen. $R_2$ preferably is phenyl optionally substituted as defined above. $R_3$ preferably is unsubstituted phenyl. $R_4$ preferably is alkoxy as defined above. $R_5$ preferably is optionally substituted alkyl as defined above. m preferably is 2. n preferably is 1 or 2, especially 2. p preferably is 2 or 3, especially 3.

Pyridinyl preferably is pyridin-2-yl; it preferably is unsubstituted or monosubstituted, preferably in 5-position. Pyrimidinyl preferably is pyrimidin-2-yl. It preferably is unsubstituted or monosubstituted, preferably in 4-position. Preferred as substitutents for pyridinyl and pyrimidinyl are halogen, cyano and nitro, especially chlorine.

When it is substituted, phenyl preferably is monosubstituted; it preferably is substituted with halogen, preferably chlorine, or methoxy. It preferably is substituted in 2-, 4- and/or 5-position, especially in 4-position.

$(C_{3-12})$cycloalkyl preferably is cyclopentyl or cyclohexyl. When it is substituted, it preferably is substituted with hydroxymethyl. $(C_{1-4})$alkoxy preferably is of 1 or 2 carbon atoms, it especially is methoxy. $(C_{2-4})$alkoxy preferably is of 3 carbon atoms, it especially is isopropoxy. Halogen is fluorine, chlorine, bromine or iodine, preferably fluorine, chlorine or bromine, especially chlorine. $(C_{1-8})$alkyl preferably is of 1 to 6, preferably 1 to 4 or 3 to 5, especially of 2 or 3 carbon atoms, or methyl. $(C_{1-4})$ alkyl preferably is methyl or ethyl, especially methyl. $(C_{1-3})$hydroxyalkyl preferably is hydroxymethyl.

A [3.1.1]bicyclic carbocyclic moiety optionally substituted as defined above preferably is bicyclo[3.1.1]hept-2-yl optionally disubstituted in 6-position with methyl, or bicyclo [3.1.1]hept-3-yl optionally trisubstituted with one methyl in 2-position and two methyl groups in 6-position. A [2.2.1] bicyclic carbocyclic moiety optionally substituted as defined above preferably is bicyclo[2.2.1]hept-2-yl.

Naphthyl preferably is 1-naphthyl. Cyclohexene preferably is cyclohex-1-en-1-yl. Adamantyl preferably is 1- or 2-adamantyl.

A pyrrolidinyl or piperidinyl moiety optionally substituted as defined above preferably is pyrrolidin-3-yl or piperidin-4yl. When it is substituted it preferably is N-substituted.

A preferred group of compounds of the invention is the compounds of formula I wherein R is R' (compounds Ia), whereby R' is:

$R_1'NH(CH_2)_2$- wherein $R_1'$ is pyridinyl optionally mono- or independently disubstituted with halogen, trifluoromethyl, cyano or nitro; or unsubstituted pyrimidinyl;

$(C_{3-7})$cycloalkyl optionally monosubstituted in 1-position with $(C_{1-3})$hydroxyalkyl;

$R_4'(CH_2)_3$- wherein $R_4'$ is $(C_{2-4})$alkoxy; or $R_5$, wherein $R_5$ is as defined above;

in free form or in acid addition salt form.

More preferred compounds of the invention are those compounds of formula I wherein R is R" (compounds Ib), whereby R" is:

$R_1"NH(CH_2)_2$- wherein $R_1"$ is pyridinyl mono- or independently disubstituted with halogen, trifluoromethyl, cyano or nitro;

$(C_{4-6})$cycloalkyl monosubstituted in 1-position with $(C_{1-3})$hydroxyalkyl;

$R_4'(CH_2)_3$- wherein $R_4'$ is as defined above; or $R_5'$ wherein $R_5'$ is a [2.2.1]- or [3.1.1]bicyclic carbocyclic moiety optionally mono- or plurisubstituted with $(C_{1-8})$alkyl; or adamantyl;

in free form or in acid addition salt form.

Even more preferred compounds of the invention are the compounds of formula I wherein R is R'" (compounds Ic), whereby R'" is:

$R_1"NH(CH_2)_2$- wherein $R_1"$ is as defined above;

$(C_{4-6})$cycloalkyl monosubstituted in 1-position with hydroxymethyl;

$R_4'(CH_2)_3$- wherein $R_4'$ is as defined above; or $R_5"$ wherein $R_5"$ is adamantyl;

in free form or in acid addition salt form.

A further group of compounds of the invention is compounds Ip, wherein R is $R^p$, which is:

a) $R_1^pNH(CH_2)_2$- wherein $R_1^p$ is a pyridinyl or pyrimidinyl moiety optionally mono- or independently disubstituted with halogen, trifluoromethyl, cyano or nitro;

b) $(C_{3-7})$cycloalkyl optionally monosubstituted in 1-position with $(C_{1-3})$hydroxyalkyl;

c) $R_2^p(CH_2)_2$- wherein $R_2^p$ is phenyl optionally mono- or independently di- or independently trisubstituted with halogen or $(C_{1-3})$alkoxy;

d) $(R_3^p)_2CH(CH_2)_2$- wherein each $R_3^p$ independently is phenyl optionally monosubstituted with halogen or $(C_{1-3})$alkoxy;

e) $R_4(CH_2)_3$- wherein $R_4$ is as defined above; or f) isopropyl optionally monosubstituted in 1-position with $(C_{1-3})$hydroxyalkyl;

in free form or in pharmaceutically acceptable acid addition salt form.

A further group of compounds of the invention is compounds Is, wherein R is $R^s$, which is:

a) $R_1^sR_{1a}^s(CH_2)_{ms}$- wherein $R_1^s$ is pyridinyl optionally mono- or independently disubstituted with chlorine, trifluoromethyl, cyano or nitro; pyrimidinyl optionally monosubstituted with chlorine or trifluoromethyl; or phenyl; $R_{1a}^s$ is hydrogen or methyl; and ms is 2or3;

b) $(C_{3-12})$cycloalkyl optionally monosubstituted in 1-position with hydroxymethyl;

c) $R_2^s(CH_2)_{ms}$- wherein either
$R_2^s$ is phenyl optionally mono- or independently di- or independently trisubstituted with halogen, alkoxy of 1 or 2 carbon atoms or phenylthio monosubstituted in the phenyl ring with hydroxymethyl; $(C_{1-6})$alkyl; 6,6-dimethylbicyclo[3.1.1]hept-2-yl; pyridinyl; naphthyl; cyclohexene; or adamantyl; and
ns is 1 to 3; or
$R_2^s$ is phenoxy; and ns is 2;

d) (3,3-diphenyl)propyl;

e) $R_4^s(CH_2)_{ps}$wherein $R_4^s$ is 2-oxopyrrolidin-1-yl or isopropoxy and ps is2or3;

f) isopropyl optionally monosubstituted in 1-position with hydroxymethyl;

g) $R_5^s$ wherein $R_5^s$ is: indanyl; a pyrrolidinyl or piperidinyl moiety optionally N-substituted with benzyl; bicyclo[2.2.1]hept-2-yl; 2,6,6trimethylbicyclo-[3.1.1] hept-3-yl; adamantyl; or $(C_{1-8})$alkyl optionally mono- or independently disubstituted with hydroxy, hydroxymethyl or phenyl;

in free form or in acid addition salt form.

The compounds of the invention may be prepared by a process which comprises coupling a reactive (2-cyanopyrrolidino)carbonylmethylene compound with an appropriate substituted amine; more particularly, for the preparation of the compounds of formula I it comprises reacting a compound of formula II

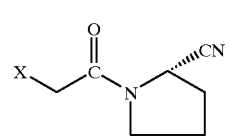

II wherein X is a reactive group,
with a compound of formula III $NH_2R$     III wherein R is as defined above,
and recovering the resultant compound of formula I in free form or in acid addition salt form.

X preferably is a halogen such as bromine, chlorine or iodine.

The process of the invention may be effected in conventional manner.

The compound of formula II is preferably reacted with at least 3 equivalents of a primary amine of formula III. The reaction is conveniently conducted in the presence of an inert, organic solvent, preferably a cyclic ether such as tetrahydrofuran. The temperature preferably is of from about 0° to about 35° C., preferably between about 0° and about 25° C.

The compounds of the invention may be isolated from the reaction mixture and purified in conventional manner, e.g. by chromatography.

The starting materials may also be prepared in conventional manner.

The compounds of formula II may e.g. be prepared by the following two-step reaction scheme:

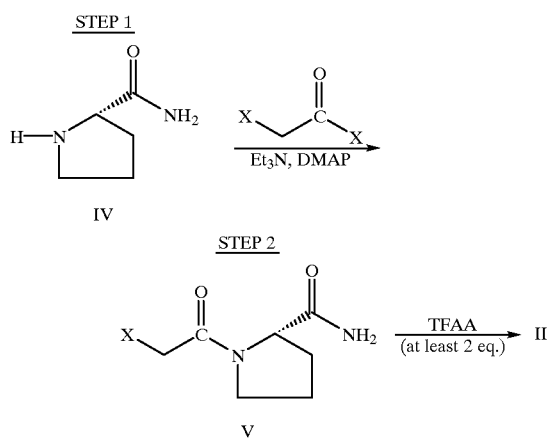

Step 1 involves the reaction of the pyrrolidine of formula IV with a slight molar excess of a haloacetylhalide such as bromoacetylbromide or chloroacetylchloride and triethylamine and a catalytic amount of dimethylaminopyridine (DMAP). The reaction conveniently is conducted in the presence of an inert, organic solvent, preferably a chlorinated, aliphatic hydrocarbon such as methylene chloride, at a temperature of from about 0° to about 25° C., preferably at a temperature between about 0° and about 15° C.

Step 2 concerns the dehydration of the compound of formula V, prepared in Step 1, with at least 2 equivalents of trifluoroacetic anhydride (TFAA). The dehydration preferably is conducted in the presence of an inert, organic solvent such as tetrahydrofuran or a chlorinated, aliphatic hydrocarbon such as methylene chloride, at a temperature of from about 0° to about 25° C., preferably at a temperature between about 0° and about 15° C.

Insofar as its preparation is not particularly described herein, a compound used as starting material is known or may be prepared from known compounds in known manner or analogously to known methods or analogously to methods described in the Examples.

For example, the primary amine compounds of formula III are known and may be prepared by procedures documented in the literature. More particularly,: a) 1-hydroxymethylcyclopentylamine can be prepared by the reduction of 1-amino-1-cyclopentane carboxylic acid with lithium aluminum hydride as set forth below:

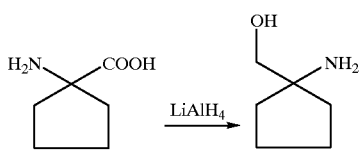

The reduction is conducted in the presence of an inert, organic solvent, preferably a cyclic ether such as tetrahydrofuran, at the reflux temperature of the solvent for a period of between 14 and 24 hours. (b) 2-[(5-chloropyridin-2-yl)amino]ethylamine can be prepared by refluxing a mixture of 2,5-dichloropyridine with ethylenediamine in an oil bath for a period of between 6 and 12 hours. (c) Similarly, 2-[(5-trifluoromethylpyridin-2-yl)amino]ethylamine can be prepared by refluxing a mixture of 2-chloro-5-trifluoromethyl pyridine with ethylenediamine in an oil bath for a period of between 6 and 12 hours. (d) 2-[(5-cyanopyridin-2-yl)amino]-ethylamine can be prepared by stirring a mixture of 2-chloropyridine-5-carbonitrile and ethylenediamine at a temperature between 20° and 30° C., for a period of between 4 and 6 hours. (e) 2-[(pyrimidin-2-yl)amino]ethylamine can be prepared by adding ethylenediamine to ice-bath cooled 2-chloropyrimidine and allowing the mixture to react at a temperature between 20° and 30° C., for a period of between 12 and 20 hours. (f) 1-amino-1-cyclohexanemethanol can be prepared by the reduction of 1-amino-1-cyclohexane carboxylic acid with lithium aluminum hydride. The reduction is conducted in the presence of an inert, organic solvent, preferably a cyclic ether such as tetrahydrofuran, at the reflux temperature of the solvent for a period of between 14 and 24 hours. (g) 2(3-aminopropylamino)-5-cyanopyridine can be prepared by refluxing a mixture of 2,5-dichloropyridine with 1,3 propyl diamine in an oil bath for a period of between 6 and 12 hours. Alternatively, the above examples (a) through (g) may be carried out at room temperature.

The instant invention also includes pharmaceutical compositions useful in inhibiting DPP-IV comprising a pharmaceutically acceptable carrier or diluent and a therapeutically effective amount of a compound of formula 1, or a pharmaceutically acceptable acid addition salt thereof.

In still another embodiment, the instant invention provides a method of inhibiting DPP-IV comprising administering to a mammal in need of such treatment a therapeutically effective amount of a compound of formula I, or a pharmaceutically acceptable acid addition salt thereof.

In a further embodiment, the instant invention provides a method of treating conditions mediated by DPP-IV inhibition comprising administering to a mammal in need of such treatment a therapeutically effective amount of a compound of formula I above, or a pharmaceutically acceptable acid addition salt thereof.

As indicated above, all of the compounds of formula 1, and their corresponding pharmaceutically acceptable acid addition salts, are useful in inhibiting DPP-IV. The ability of the compounds of formula I, and their corresponding pharmaceutically acceptable acid addition salts, to inhibit DPP-IV may be demonstrated employing the Caco-2 DPP-IV Assay which measures the ability of test compounds to inhibit DPP-IV activity from human colonic carcinoma cell extracts. The human colonic carcinoma cell line Caco-2 was obtained from the American Type Culture Collection (ATCC HTB 37). Differentiation of the cells to induce DPP-IV expression was accomplished as described by Reisher, et al. in an article entitled "Increased expression of . . . intestinal cell line Caco-2" in Proc. Natl. Acad. Sci., Vol. 90, pgs. 5757–5761 (1993). Cell extract is prepared from cells solubilized in 10 mM Tris-HCl, 0.15 M NaCl, 0.04 t.i.u. aprotinin, 0.5% nonidet-P40, pH 8.0, which is centrifuged at 35,000 g for 30 min. at 4° C. to remove cell debris. The assay is conducted by adding 20 μg solubilized Caco-2 protein, diluted to a final volume of 125 pi in assay buffer (25 mM Tris-HCl pH 7.4, 140 mM NaCl, 10 mM KCl, 1% bovine serum albumin) to microtiter plate wells. The reaction is initiated by adding 25 μl of 1 mM substrate (H-Alanine-Proline-pNA; pNA is p-nitroaniline). The reaction is run at room temperature for 10 minutes after which time a 19 μl volume of 25% glacial acetic acid is added to stop the reaction. Test compounds are typically added as 30 μl additions and the assay buffer volume is reduced to 95 μl. A standard curve of free p-nitroaniline is generated using 0–500 μM solutions of free pNA in assay buffer. The curve generated is linear and is used for interpolation of substrate consumption (catalytic activity in nmoles substrate cleaved/min). The endpoint is determined by measuring absorbance at 405 nm in a Molecular Devices UV Max microfiter plate reader. The potency of the test compounds as DPP-IV inhibitors, expressed as IC-$_{50}$, is calculated from 8-point, dose-response curves using a 4-parameter logistic function.

The following IC$_{50}$s were obtained:

| Compound | Caco-2 DPP-IV (nM) |
| --- | --- |
| Ex. 1 | 36 |
| Ex. 2 | 176 |
| Ex. 3 | 22 |
| Ex. 4 | 140 |
| Ex. 5 | 26 |
| Ex. 6 | 50 |
| Ex. 7A | 165 |
| Ex. 8 | 8 |
| Ex. 7B | 175 |
| Ex. 9A | 990 |
| Ex. 7C | 290 |
| Ex. 9C | 295 |
| Ex. 10 | 54 |
| Ex. 11 | 215 |
| Ex. 7D | 382 |
| Ex. 7E | 388 |
| Ex. 12 | 279 |
| Ex. 13 | 227 |
| Ex. 14 | 110 |
| Ex. 15 | 150 |
| Ex. 16 | 130 |
| Ex. 17 | 60 |
| Ex. 18 | 100 |
| Ex. 19 | 120 |
| Ex. 20 | 90 |
| Ex. 21 | 390 |
| Ex. 22 | 150 |
| Ex. 23 | 50 |
| Ex. 24 | 70 |
| Ex. 25 | 140 |
| Ex. 26 | 170 |
| Ex. 27 | 310 |
| Ex. 28 | 90 |
| Ex. 29 | 130 |
| Ex. 30 | 650 |
| Ex. 31 | 500 |
| Ex. 32 | 150 |
| Ex. 33 | 10 |
| Ex. 34 | 37 |
| Ex. 35 | 130 |
| Ex. 36 | 160 |
| Ex. 37 | 220 |
| Ex. 38 | 50 |
| Ex. 39 | 380 |
| Ex. 40 | 240 |
| Ex. 41 | 140 |
| Ex. 42 | 240 |
| Ex. 43 | 850 |
| Ex. 44 | 5 |
| Ex. 45 | 700 |
| Ex. 46 | 150 |
| Ex. 47 | 10 |
| Ex. 48 | 35 |
| Ex. 49 | 12 |
| Ex. 50 | 23 |
| Ex. 51 | 250 |
| Ex. 52 | 20 |
| Ex. 53 | 860 |
| Ex. 54 | 240 |
| Ex. 55 | 270 |
| Ex. 56 | 350 |
| Ex. 57 | 470 |
| Ex. 58 | 50 |
| Ex. 59 | 390 |
| Ex. 60 | 600 |
| Ex. 61 | 310 |
| Ex. 62 | 270 |
| Ex. 63 | 46 |
| Ex. 64 | 220 |
| Ex. 65 | 80 |
| Ex. 66 | 60 |

The ability of the compounds of formula I, and their corresponding pharmaceutically acceptable acid addition salts, to inhibit DPP-IV may also be demonstrated by measuring the effects of test compounds on DPP-IV activity in human and rat plasma employing a modified version of the assay described by Kubota, et al. in an article entitled "Involvement of dipeptidylpeptidase IV in an in vivo immune response" in Clin. Exp. Immunol., Vol. 89, pgs. 192–197 (1992). Briefly, five μl of plasma are added to 96-well flat-bottom mictotiter plates (Falcon), followed by the addition of 5 μl of 80 mM MgCl$_2$ in incubation buffer (25 mM HEPES, 140 mM NaCl, 1% RIA-grade BSA, pH 7.8). After a 5 min. incubation at room temperature, the reaction is initiated by the addition of 10 μl of incubation buffer containing 0.1 mM substrate (H-Glycine-Proline-AMC; AMC is 7-amino4-methylcoumarin). The plates are covered with aluminum foil (or kept in the dark) and incubated at room temperature for 20 min. After the 20 min. reaction, fluorescence is measured using a CytoFluor 2350 fluorimeter (Excitation 380 nm Emission 460 nm; sensitivity setting 4). Test compounds are typically added as 2 μl additions and the assay buffer volume is reduced to 13 μl. A fluorescence-concentration curve of free AMC is generated using 0–50 μM solutions of AMC in assay buffer. The curve generated is linear and is used for interpolation of substrate consumption (catalytic activity in nmoles substrate cleaved/min). As with the previous assay, the potency of the test compounds as DPP-IV inhibitors, expressed as IC$_{50}$, is calculated from 8-point, dose-response curves using a 4 parameter logistic function.

The following IC$_{50}$s were obtained:

| Compound | human plasma DPP-IV (nM) | rat plasma DPP-IV (nM) |
| --- | --- | --- |
| Ex. 1 | 27 | 22 |
| Ex. 3 | 7 | 6 |
| Ex. 4 | 40 | 23 |
| Ex. 5 | 37 | 18 |
| Ex. 6 | 22 | 32 |
| Ex. 8 | 12 | 11 |
| Ex. 10 | 51 | 19 |
| Ex. 12 | 95 | 38 |

-continued

| Compound | human plasma DPP-IV (nM) | rat plasma DPP-IV (nM) |
| --- | --- | --- |
| Ex. 14 | 95 | 24 |
| Ex. 15 | 70 | 40 |
| Ex. 16 | 170 | 60 |
| Ex. 17 | 250 | 120 |
| Ex. 18 | 160 | 70 |
| Ex. 19 | 180 | 50 |
| Ex. 20 | 180 | 150 |
| Ex. 21 | 210 | 110 |
| Ex. 22 | 170 | 60 |
| Ex. 23 | 40 | 40 |
| Ex. 24 | 32 | 19 |
| Ex. 25 | 110 | 140 |
| Ex. 26 | 240 | 70 |
| Ex. 27 | 150 | 160 |
| Ex. 28 | 180 | 60 |
| Ex. 29 | 28 | 9 |
| Ex. 30 | 80 | 90 |
| Ex. 31 | 80 | 100 |
| Ex. 32 | 160 | 130 |
| Ex. 33 | 20 | 10 |
| Ex. 34 | 277 | 161 |
| Ex. 35 | 1090 | 340 |
| Ex. 36 | 170 | 80 |
| Ex. 37 | 100 | 150 |
| Ex. 38 | 65 | 23 |
| Ex. 39 | 220 | 200 |
| Ex. 40 | 340 | 370 |
| Ex. 41 | 100 | 50 |
| Ex. 42 | 140 | 180 |
| Ex. 43 | 240 | 120 |
| Ex. 44 | 10 | 10 |
| Ex. 45 | 2130 | 390 |
| Ex. 46 | 280 | 60 |
| Ex. 47 | 11 | 5 |
| Ex. 48 | 60 | 30 |
| Ex. 49 | 8 | 3 |
| Ex. 50 | 60 | 40 |
| Ex. 51 | 180 | 150 |
| Ex. 52 | 20 | 10 |
| Ex. 53 | 490 | 400 |
| Ex. 54 | 90 | 60 |
| Ex. 55 | 140 | 90 |
| Ex. 56 | 140 | 100 |
| Ex. 57 | 420 | 150 |
| Ex. 58 | 20 | 100 |
| Ex. 59 | 280 | 130 |
| Ex. 60 | 250 | 110 |
| Ex. 61 | 260 | 80 |
| Ex. 62 | 190 | 100 |
| Ex. 63 | 60 | 30 |
| Ex. 64 | 150 | 60 |
| Ex. 65 | 90 | 40 |
| Ex. 66 | 130 | 40 |

In view of their ability to inhibit DPP-IV, the compounds of formula I, and their corresponding pharmaceutically acceptable acid addition salts, are useful in treating conditions mediated by DPP-IV inhibition. Based on the above and findings in the literature, it is expected that the compounds disclosed herein are useful in the treatment of conditions such as non-insulin-dependent diabetes mellitus, arthritis, obesity, allograft transplantation, and calcitonin-osteoporosis. More specifically, for example, the compounds of formula I, and their corresponding pharmaceutically acceptable acid addition salts, improve early insulin response to an oral glucose challenge and, therefore, are useful in treating non-insulin-dependent diabetes mellitus. The ability of the compounds of formula I, and their corresponding pharmaceutically acceptable acid addition salts, to improve early insulin response to an oral glucose challenge may be measured in insulin resistant rats according to the following method:

Male Sprague-Dawley rats that had been fed a high fat diet (saturated fat=57% calories) for 2–3 weeks were fasted for approximately 2 hours on the day of testing, divided into groups of 8–10, and dosed orally with 10 µmol/kg of the test compounds in CMC. An oral glucose bolus of 1g/kg was administered 30 minutes after the test compound directly into the stomach of the test animals. Blood samples, obtained at various timepoints from chronic jugular vein catheters were analyzed for plasma glucose and immunoreactive insulin (IRI) concentrations, and plasma DPP-IV activity. Plasma insulin levels were assayed by a double antibody radioimmunoassay (RIA) method using a specific anti-rat insulin antibody from Linco Research (St. Louis, Mo.). The RIA has a lower limit of detection of 0.5 µU/ml with intra- and inter-assay variations of less than 5%. Data are expressed as % increase of the mean of the control animals. Upon oral administration, each of the compounds tested amplified the early insulin response which led to an improvement in glucose tolerance in the insulin resistant test animals. The following results were obtained:

| Compound | Increase of Insulin Response at 10 µmol/kg |
| --- | --- |
| Ex. 1 | 61% |
| Ex. 3 | 66% |
| Ex. 5 | 108% |
| Ex. 8 | 144% |
| Ex. 12 | 59% |

The precise dosage of the compounds of formula I, and their corresponding pharmaceutically acceptable acid addition salts, to be employed for treating conditions mediated by DPP-IV inhibition depends upon several factors, including the host, the nature and the severity of the condition being treated, the mode of administration and the particular compound employed. However, in general, conditions mediated by DPP-IV inhibition are effectively treated when a compound of formula I, or a corresponding pharmaceutically acceptable acid addition salt, is administered enterally, e.g., orally, or parenterally, e.g., intravenously, preferably orally, at a daily dosage of 0.002–5, preferably 0.02–2.5 mg/kg body weight or, for most larger primates, a daily dosage of 0.1–250, preferably 1–100 mg. A typical oral dosage unit is 0.01–0.75 mg/kg, one to three times a day.

Usually, a small dose is administered initially and the dosage is gradually increased until the optimal dosage for the host under treatment is determined. The upper limit of dosage is that imposed by side effects and can be determined by trial for the host being treated.

The compounds of formula I, and their corresponding pharmaceutically acceptable acid addition salts, may be combined with one or more pharmaceutically acceptable carriers and, optionally, one or more other conventional pharmaceutical adjuvants and administered enterally, e.g., orally, in the form of tablets, capsules, caplets, etc. or parenterally, e.g., intravenously, in the form of sterile injectable solutions or suspensions. The enteral and parenteral compositions may be prepared by conventional means.

The compounds of formula I, and their corresponding pharmaceutically acceptable acid addition salts, may be formulated into enteral and parenteral pharmaceutical compositions containing an amount of the active substance that is effective for treating conditions mediated by DPP-IV inhibition, such compositions in unit dosage form and such compositions comprising a pharmaceutically acceptable carrier.

The compounds of formula I (including those of each of the subscopes thereof and each of the examples) may be administered in enantiomerically pure form (e.g., ee≧98%, preferably ≧99%) or together with the R enantiomer, e.g., in racemic form. The above dosage ranges are based on the compounds of formula I (excluding the amount of the R enantiomer).

Prior US Provisional Application number 60/030,570, filed on Nov. 7, 1996 is incorporated by reference herein, in it's entirety.

The following examples show representative compounds encompassed by this invention and their synthesis. However, it should be clearly understood that they are for purposes of illustration only.

EXAMPLE 1

1-[2-[(5-chloropyridin-2-yl)amino]ethylamino] acetyl-2-cyano-(S)-pyrrolidine dihydrochloride A. Preparation of 2-carbamoylpyrrolidine-carbonylmethylene-(S)-bromide 22.37 g (196 mmol) of (S)-2-carbamoylpyrrolidine, 30.1 ml (216 mmol) of triethylamine and 30.0 mg of dimethylaminopyridine (DMAP) are dissolved in 200 ml of methylene chloride and the solution is then added, dropwise, to an ice-cold solution of 18.8 ml (216 mmol) of bromoacetylbromide in 192 ml of methylene chloride, over a period of 60 minutes under a calcium sulfate drying tube. The resultant solution is then stirred for 2 hours at ice-water temperature under a calcium sulfate dying tube, after which time it is poured into 3.5 liters of ethyl acetate. The resultant precipitate is filtered, washed with ethyl acetate, and the filtrate is concentrated to obtain the desired compound as a bard yellow taffy.

B. Preparation of 2-Cyanopyrrolidino-Carbonylmethylene-(S)Bromide 50.0 g (213 mmol) of the bromide compound prepared in a) above is dissolved in 300 ml of methylene chloride and the solution is cooled in an ice water bath under a calcium sulfate drying tube. The cooled solution is then poured into 60.2 ml (426 mmol) of trifluoroacetic anhydride over a 2 minute period and the resultant solution is then stirred at ice-water temperature under a calcium sulfate drying tube for 4 hours and partitioned between methylene chloride and saturated aqueous sodium bicarbonate. The product is then extracted into the methylene chloride layer and the aqueous layer is then washed twice with methylene chloride. The combined organic layers are then washed successively with water and brine and then dried over sodium sulfate. The solution is then filtered and the solvent is removed by rotovaping and high vacuum pumping to obtain the desired compound as a dark yellow solid.

C. Preparation of the Title Compound in Free Base Form

To a 500 ml flask is added 16.6g (97.2 mmol) of 2-[(5-chloropyridin-2-yl)amino]ethylamine and 100 ml of tetrahydrofuran and the mixture is cooled in an ice bath. To the cooled mixture is added 7.0 g (32.4 mmol) of the bromide compound prepared in b) above dissolved in 30 ml of tetrahydrofuran. The resultant mixture is stirred for 2 hours at 0° C., the solvent is removed by rotovaping and the mixture is partitioned between ethyl acetate and water. The product is then extracted into the ethyl acetate layer and the aqueous layer is then washed twice with ethyl acetate. The combined organic layers are then washed successively with water and brine, dried over sodium sulfate and concentrated to obtain the desired compound in crude form. The crude form is then purified on silica gel employing a mixture of 5% methanol in methylene chloride as the eluent to yield the desired compound as a light brown oil.

D. Preparation of the Title Compound

After dissolving the free base compound prepared in c) above in 30 ml of dry tetrahydrofuiran, hydrogen chloride gas is bubbled into the solution for five seconds. The off-white precipitate that forms is then filtered, washed with dry tetrahydrofuran and the solvent is removed by high vacuum pumping to obtain the title compound as an off-white solid, m.p. 265°–267° C.

EXAMPLE 2

1-[2-[(5-trifluoromethylpryrdin-2-yl)amino] ethylamino]acetyl-2-cyano-(S)-pyrrolidine To a 25 ml. flask is added 1.15 g (5.61 mmol) of 2-[(5-trifluoromethylpyrdin-2-yl)-amino]ethylamine and 10 ml of tetrahydrofuran and the mixture is cooled in an ice bath. To the cooled mixture is added 0.404 g (1.87 mmol) of the bromide compound of Example 1b) dissolved in 5 ml of tetrahydrofuran. The resultant mixture is stirred for 2 hours at 0° C., the solvent is removed by rotovaping and the mixture is partitioned between ethyl acetate and water. The product is then extracted into the ethyl acetate layer and the aqueous layer is then washed twice with ethyl acetate. The combined organic layers are then washed successively with water and brine, dried over sodium sulfate and concentrated to obtain the desired compound in crude form. The crude form is then purified on silica gel employing a mixture of 5% methanol in methylene chloride as the eluent to yield the title compound as a golden oil.

EXAMPLE 3

1-[2-[(5-cyanopyridin-2-yl)amino]ethylamino] acetyl-2-cyano-S)-pyrrolidine dihydrochloride A. Preparation of the Title Compound in Free Base Form Following essentially the procedure of Example 1c), and using in place of the amine therein, an equivalent amount of 2-[(5-cyanopyridin-2-yl)amino]-ethylamine, the desired compound is obtained as a golden oil.

B. Preparation of the Title Compound

Following essentially the procedure of Example 1d), and using in place of the free base compound prepared in Example 1c), an equivalent amount of the free base compound prepared in a) above, the title compound is obtained as an off-white precipitate, m.p. 155°–157° C.

EXAMPLE 4

1[-2-[(pyrimidin-2-yl)amino]ethylamino]acetyl-2-cyano-(S)-pyrrolidine

Following essentially the procedure of Example 2, and using in place of the amine therein, an equivalent amount of 2-[(pyrimidin-2-yl)amino]ethylamine, and using in place of the eluent therein, a mixture of 10% methanol in methylene chloride, the title compound is obtained as a golden oil.

EXAMPLE 5

1-[(1-hydroxymethylcyclopent-1-yl)amino]acetyl-2-cyano-(S)-pyrrolidine

To 1.5 g of (1-hydroxymethyl)cyclopentylamine in 40 ml of anhydrous tetrahydrofuran is added, dropwise via an addition funnel over 40 minutes, 0.93 g (4.35 mmol) of the bromide compound of Example 1b) under a calcium sulfate drying tube. The resultant mixture is then stirred at room temperature for 18 hours under a calcium sulfate drying tube, after which time hydrogen chloride gas is bubbled in for ~5 seconds. The resultant gum is then separated from the solution by decanting and washed with 25 ml of tetrahydrofuran. The solution is then decanted and the gum is partitioned between methylene chloride and saturated aqueous sodium bicarbonate. The product is then extracted into the methylene chloride layer and the aqueous layer is then washed twice with methylene chloride. The combined organic layers are then washed successively with water and brine and then dried over sodium sulfate. The solution is then filtered and the solvent is removed by rotovaping and high vacuum pumping to obtain the title compound as a clear yellow oil which solidifies to a yellow solid, m.p. 65°–67° C.

EXAMPLE 6

1-[2-[(pyridin-2-yl)amino]ethylamino]acetyl-2-cyano(S)-pyrrolidine

Following essentially the procedure of Example 2, and using in place of the amine therein, an equivalent amount of 2-[(pyridin-2-yl)amino]ethylamine, and using in place of the eluent therein, a 90:10:0.5 mixture of methylene chloride, methanol and ammonium hydroxide, the title compound is obtained as a golden oil.

EXAMPLE 7

Following essentially the procedure of Example 2, and using in place of the amine therein, an equivalent amount of:
  a) 2-[(4-chloropyrimidin-2-yl)amino]ethylamine;
  b) 2-[(3-chloropyridin-2-yl)amino]ethylamine;
  c) 2-[(4-trifluoromethylpyrimidin-2-yl)amino]ethylamine;
  d) (2-chlorophenyl)ethylamine; and
  e) (3,3-biphenyl)propylamine;
there is obtained:
  A) 1-[2-[(4-chloropyrimidin-2-yl)amino]ethylamino]acetyl-2-cyano-(S)-pyrrolidine as a tan solid;
  B) 1-[2-[(3-chloropyridin-2-yl)amino]ethylamino]acetyl-2-cyano-(S)-pyrrolidine as a golden oil;
  C) 1-[2-[4-trifluoromethylpyrimidin-2-yl)amino]ethylamino]acetyl-2-cyano-(S)-pyrrolidine as a golden oil;
  D) 1-[(2-chlorophenyl)ethylamino]acetyl-2-cyano-(S)-pyrrolidine; and
  E) 1-[(3,3-diphenyl)propylamino]acetyl-2-cyano-(S)-pyrrolidine, respectively.

EXAMPLE 8

1-[2-[(5-nitropyridin-2-yl)amino]ethylamino]acetyl-2-cyano-(S)pyrrolidine

To 83.6 ml of anhydrous tetrahydrofuran is added 4.54 g (24.9 mmol) of 2-[(5-nitropyridin-2-yl)amino]ethylamine, and the resultant mixture is heated slightly then stirred at room temperature under a calcium sulfate drying tube. 1.80 g (8.3 mmol) of the bromide compound of Example 1b) in 20 ml of anhydrous tetrahydrofuran is then added, over a period of 30 minutes, under a calcium sulfate drying tube. The resultant mixture is then stirred at room temperature for 2 hours under a calcium sulfate drying tube and concentrated via rotovaping. The resultant paste is then partitioned between methylene chloride and saturated aqueous sodium bicarbonate. The product is then extracted into the methylene chloride layer and the aqueous layer is then washed twice with methylene chloride. The combined organic layers are then washed successively with water and brine and then dried over sodium sulfate. The solution is then filtered and the solvent is removed by rotovaping and high vacuum pumping to obtain the crude form of the title compound as a dark yellow-orange clear thick oil. The crude form is then flash chromatographed employing a mixture of 5% methanol in methylene chloride as the eluent to obtain the title compound as a bright yellow thick oil.

EXAMPLE 9

Following essentially the procedure of Example 2, and using in place of the amine therein, an equivalent amount of:
  a) 2-[(3-chloro-5-trifluoromethylpyridin-2-yl)amino]ethylamine;
  b) 2-[(3-trifluoromethylpyridin-2-yl)amino]ethylamine; and
  c) 2-[(3,5-dichloropyridin-2-yl)amino]ethylamine;
and using in place of the eluent therein, a mixture of 3% methanol in methylene chloride, there is obtained:
  A) 1-[2-[(3-chloro-5-trifluoromethylpyridin-2-yl)amino]ethylamino]acetyl-2-cyano-(S)-pyrrolidine as a golden oil;
  B) 1-[2-[(3-trifluoromethylpyridin-2-yl)amino]ethylamino]acetyl-2-cyano-(S)pyrrolidine as a golden oil; and
  C) 1-[2-[(3,5-dichloropyridin-2-yl)amino]ethylamino]acetyl-2-cyano-(S)-pyrrolidine as a golden oil.

EXAMPLE 10

1-[(cyclopent-1-yl)amino-acetyl-2-cyano-(S)-pyrrolidine monohydrochloride

A. Preparation of the Title Compound in Free Base Form

Following essentially the procedure of Example 2, and using in place of the amine therein, an equivalent amount of (cyclopent-1-yl)amine, the desired compound is obtained as a tan solid.

B. Preparation of the Title Compound

Following essentially the procedure of Example 1d), and using in place of the free base compound therein, an equivalent amount of the compound prepared in a) above, the title compound is obtained as a white solid.

EXAMPLE 11

1-[2-(2-bromo4,5-dimethoxyphenyl)ethylamino]acetyl-2-cyano-(S)-pyrrolidine

To 15 ml of anhydrous tetrahydrofuran is added 1.44 g (5.52 mmol) of 2-(2-bromo4,5-dimethoxy)ethylamine, and the resultant mixture is heated slightly under a calcium sulfate drying tube. 0.4 g (1.84 mmol) of the bromide compound of Example 1b) is then added, dropwise, over a period of 10 minutes. The resultant mixture is then stirred at room temperature for 18 hours under a calcium sulfate drying tube, concentrated via rotovaping and partitioned between methylene chloride and saturated aqueous sodium bicarbonate. The product is then extracted into the methylene chloride layer and the aqueous layer is then washed twice with methylene chloride. The combined organic layers are then washed successively with water and brine and then dried over sodium sulfate. The solution is then filtered and the solvent is removed by rotovaping and high vacuum pumping to obtain the crude form of the title compound as a clear yellow oil. The crude form is then flash chromatographed employing a mixture of 5% methanol in methylene chloride as the eluent to obtain the title compound as a clear, light yellow, thick oil.

EXAMPLE 12

1-[3-(isopropoxy)propylamino]acetyl-2-cyano-(S)-pyrrolidine monohydrochloride A. Preparation of the Title Compound in Free Base Form Following essentially the procedure of Example 1c), and using in place of the amine therein, an equivalent amount of 3-(isopropoxy)propylamine, the desired compound is obtained as a brown oil.

B. Preparation of the Title Compound

Following essentially the procedure of Example 1d), and using in place of the free base compound therein, an equivalent amount of the compound prepared in a) above, the title compound is obtained as a white solid, m.p. 174°–176° C.

EXAMPLE 13

1-1(2-hydroxy-1,1-dimethylethylamino)]acetyl-2-cyano-(S)-pyrrolidine monohydrochloride A. Preparation of the Title Compound in Free Base Form Following essentially the procedure of Example 2, and using in place of the amine therein, an equivalent amount of 2-hydroxy-1,1-dimethylethylamine, and using in place of the eluent therein, an 80:20:1 mixture of methylene chloride, methanol and ammonium hydroxide, the title compound is obtained as a golden oil.

B. Preparation of the Title Compound

Following essentially the procedure of Example 1d), and using in place of the free base compound therein, an equivalent amount of the compound prepared in a) above, the title compound is obtained as a brown solid.

EXAMPLE 14

1-[3-(2-oxo-pyrrolidin-1-yl)propylamino]acetyl-2-cyano-(S)-pyrrolidine monohydrochloride A. Preparation of the Title Compound in Free Base Form Following essentially the procedure of Example 2, and using in place of the amine therein, an equivalent amount of 3-(2-oxo-pyrrolidin-1-yl) propylamine, and using in place of the eluent therein, a 90:10:1 mixture of methylene chloride, methanol and ammonium hydroxide, the desired compound is obtained as a golden oil.

B. Preparation of the Title Compound

Following essentially the procedure of Example 1d), and using in place of the free base compound therein, an equivalent amount of the compound prepared in a) above, the title compound is obtained as a tan solid.

Below are the $^{13}C$ NMR signals for tie nitrile functionalities of the specific synthesized compounds described above:

| Compound # | $^{13}C$ NMR (MHz, solvent) δ ppm (CN) |
|---|---|
| Ex. 5 | $^{13}C$ NMR (75 MHz, CD$_3$OD) δ 119.64 ppm (CN) |
| Ex. 12 | $^{13}C$ NMR (75 MHz, D$_2$O) δ 121.63 ppm (CN) |
| Ex. 1 | $^{13}C$ NMR (75 MHz, D$_2$O) δ 121.60 ppm (CN) |
| Ex. 3 | $^{13}C$ NMR (75 MHz, D$_2$O) δ 120.42 ppm (CN) |
| Ex. 8 | $^{13}C$ NMR (75 MHz, DMSO) δ 119.13 ppm (CN) |
| Ex. 7B | $^{13}C$ NMR (75 MHz, CDCl$_3$) δ 118.23 ppm (CN) |
| Ex. 9A | $^{13}C$ NMR (75 MHz, CD$_3$OD) δ 119.68 ppm (CN) |
| Ex. 9B | $^{13}C$ NMR (75 MHz, CD$_3$OD) δ 119.66 ppm (CN) |
| Ex. 9C | $^{13}C$ NMR (75 MHz, CD$_3$OD) δ 119.68 ppm (CN) |
| Ex. 6 | $^{13}C$ NMR (75 MHz, CD$_3$OD) δ 119.84 ppm (CN) |
| Ex. 7C | $^{13}C$ NMR (75 MHz, CDCl$_3$) δ 118.23 ppm (CN) |
| Ex. 2 | $^{13}C$ NMR (75 MHz, CD$_3$OD) δ 119.68 ppm (CN) |
| Ex. 7A | $^{13}C$ NMR (75 MHz, CD$_3$OD) δ 119.66 ppm (CN) |
| Ex. 4 | $^{13}C$ NMR (75 MHz, CD$_3$OD) δ 119.66 ppm (CN) |
| Ex. 10 | $^{13}C$ NMR (75 MHz, D$_2$O) δ 121.69 ppm (CN) |
| Ex. 11 | $^{13}C$ NMR (75 MHz, CDCl$_3$) δ 118.31 ppm (CN) |
| Ex. 7D | $^{13}C$ NMR (75 MHz, CD$_3$OD) δ 119.63 ppm (CN) |
| Ex. 7E | $^{13}C$ NMR (75 MHz, CD$_3$OD) δ 119.64 ppm (CN) |
| Ex. 13 | $^{13}C$ NMR (75 MHz, D$_2$O) δ 121.52 ppm (CN) |
| Ex. 14 | $^{13}C$ NMR (75 MHz, D$_2$O) δ 121.52 ppm (CN) |

EXAMPLE 15

1-[(1-hydroxymethylcylohexyl)amino]acetyl-2-cyano-(S)-pyrrolidine

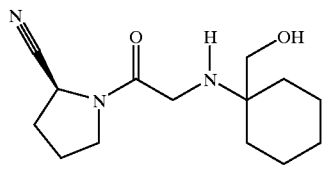

A. Preparation of 1-chloroacetyl-2-cyanopyrrolidine

To a mechanically stirred solution of 20.0 g (180.0 mmol) of chloroacetylchloride and 97 g (0.70 mmol) of potassium carbonate in 150 ml of tetrahydrofuran was added a solution of L-prolinamide 20.0 g (180.0 mmol) in 500 ml of tetrahydrofuran in a dropwise fashion over 45 minutes. This reaction was then mechanically stirred for an additional two hours. The reaction was then filtered to remove potassium salts and the filtrate was dried over Na$_2$SO$_4$. The Na$_2$SO$_4$ was then removed via filtration and to this colorless filtrate was added trifluoroacetic anhydride (25.0 ml, 0.180 mmol) in one portion. The reaction is then magnetically stirred for 1 hour and the resulting clear yellow/orange solution is concentrated via rotovap. The excess trifluoroacetic anhydride is chased by adding ethyl acetate to the concentrated oil and reconcentrating via rotovap. This operation is performed three times.

The resulting oil is partitioned between ethyl acetate and water. The product is then extracted into the ethyl acetate and the aqueous layer is then washed twice with ethyl acetate. The combined organic layers are then washed successively with water and brine dried over magnesium sulfate, filtered and concentrated to obtain 17.0 g (98.6 mmol) of 1-chloroacetyl-2-cyanopyrrolidine as a yellow solid.

B. Preparation of the Title Compound

To a 100 ml flask is dissolved 1.2 g (8.70 mmol) of 1-amino-1-cyclohexanemethanol (amine nucleophile; preparation described above) into 20 ml of tetydrofuran. Potassium carbonate (1.60 g, 11.6 mmol) is then added and the solution is cooled in an ice-water bath. To this cooled mixture is added a solution of 0.50 g (2.89 mmol) of 1-chloroacetyl-2-cyanopyrrolidine in 10 ml of tetrahydrofuran over 20 minutes. The reaction is then stirred at ice-water temperature for two hours under a calcium sulfate drying tube and then allowed to stir at room temperature for 18 hours. The reaction is then filtered with THF washing to remove the potassium salts and concentrated via rotovap to provide an opaque, light-yellow oil. The crude form is then purified on silica gel employing a mixture of 5% methanol in methylene chloride as the eluent to yield the free base of the title compound as a yellow waxy solid. Melting point= softens at 93° C. $^{13}C$ NMR(ppm)=118.1.

Using the procedures described in the above examples, and/or with minor modifications thereto as noted below, the following additional compounds were prepared:

EXAMPLE 16

Pyrrolidine, 1-[[2-(4-ethoxyphenyl)ethyl]amino]acetyl-2-cyano-,(S)-,monohydrochloride

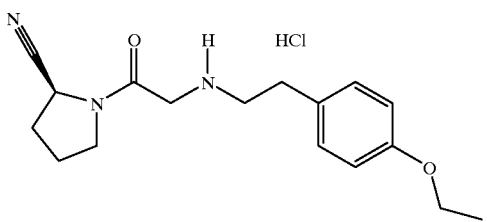

4-Ethoxyphenethylamine (commercially available) was used as the amine nucleophile. The title compound was a white solid. Melting point=182°–184° C. $^{13}$C NMR (ppm)=121.4.

EXAMPLE 17

Pyrrolidine, 1-[(1-phenylmethyl-3-pyrrolidinyl)amino]acetyl-2-cyano-,(S)-(R)-,dihydrochloride

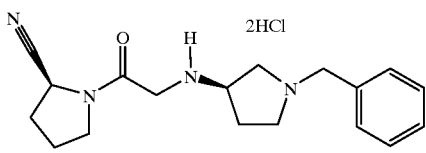

(3R)-(−)-1-Benzyl-3-aminopyrrolidine (commercially available) was used as the amine nucleophile. The title compound was an off white solid. Melting point=175° C.–177° C. $^{13}$C NMR (ppm)=121.5.

EXAMPLE 18

Pyrrolidine, 1-[[2-(4-methoxyphenyl)ethyl]amino]acetyl-2-cyano-,(S)-,monohydrochloride

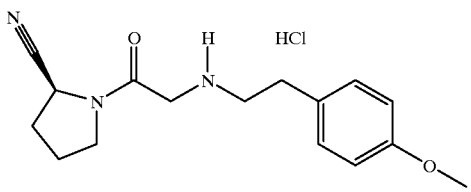

4-Methoxyphenethylamine (commercially available) was used as the amine nucleophile. The title compound was a white solid. Melting point=185° C.–187° C. $^{13}$C NMR (ppm)=121.4.

EXAMPLE 19

Pyrrolidine, 1-[[2-(3-methoxyphenyl)ethyl]amino]acetyl-2-cyano-,(S)-,monohydrochloride

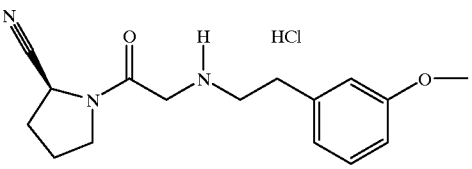

3-Methoxyphenethylamine (commercially available) was used as the amine nucleophile. The title compound was a light yellow solid. Melting point=172° C.–174° C. $^{13}$C NMR (ppm)=119.25.

EXAMPLE 20

Pyrrolidine, 1-[[(1-naphthalenyl)methyl]amino]acetyl-2-cyano-,(S)-,monohydrochloride

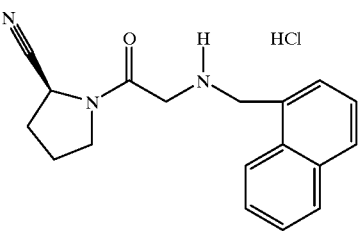

1-Naphthalenemethylamine (commercially available) was used as the amine nucleophile. The title compound was a light yellow solid. Melting point=130° C.–135° C. $^{13}$C NMR (ppm)=119.29.

EXAMPLE 21

Pyrrolidine, 1-[(3-phenylpropyl)amino]acetyl-2-cyano-,(S)-,monohydrochloride

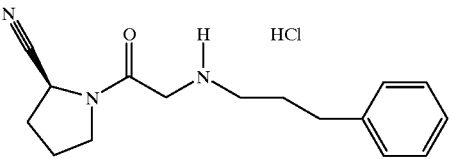

3-Phenyl-1-propylamine (commercially available) was used as the amine nucleophile. The title compound was an off-white fluffy solid. $^{13}$C NMR (ppm)=119.26.

EXAMPLE 22

Pyrrolidine, 1-[[3-[(phenyl)(methyl)amino]propyl]amino]acetyl-2-cyano-, (S)-,dihydrochloride

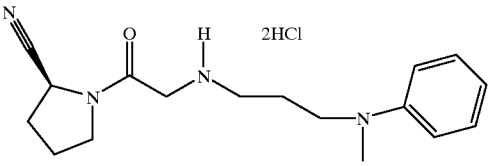

N-(3-Aminopropyl)-N-methylaniline (commercially available) was used as the amine nucleophile. The title compound was a white solid. Melting point=96° C.–98° C. (foams). $^{13}$C NMR (ppm)–121.6.

EXAMPLE 23

Pyrrolidine, 1-[2-[(3,4-dimethoxyphenyl)ethyl]amino]acetyl-2-cyano-,(S)-,monohydrochloride

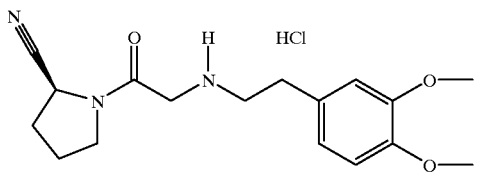

3,4-Dimethoxyphenethylamine (commercially available) was used as the amine nucleophile. The Title compound was a white solid. Melting point=170° C.–172° C. $^{13}$C NMR (ppm)=121.5.

EXAMPLE 24

Pyrrolidine, 1-(acycloheptylamino)acetyl-2-cyano-,(S)-,monohydrochloride

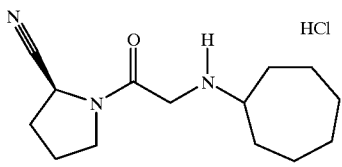

Cycloheptylamine (commercially available) was used as the amine nucleophile. The title compound was a white solid. Melting point=68° C.–70° C. $^{13}$C NMR (ppm)=121.4.

EXAMPLE 25

Pyrrolidine, 1-[[(6,6-dimethylbicyclo[3.1.1]hept-2-yl)methyl]amino]acetyl-2-cyano-[1S[1α,2α(S*),5α]]-(S)-,monohydrochloride

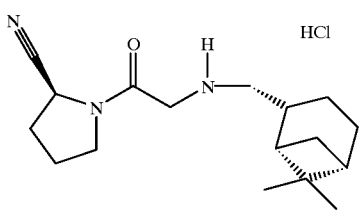

(–)-Cis-myrtanylamine (commercially available) was used as the amine nucleophile. The title compound was a white solid. Melting point=275° C.–279° C., decomposed. $^{13}$C NMR (ppm)=119.17.

EXAMPLE 26

Pyrrolidine, 1-[[2-(2,5-dmethoxyphenyl)ethyl]amino]acetyl-2-cyano-,(S)-,monohydrochloride

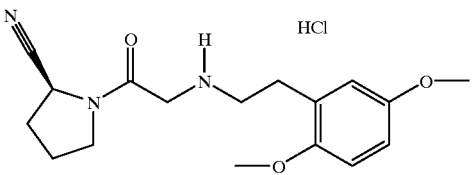

2,5-Dimethoxyphenethylamine (commercially available) was used as the amine nucleophile. The title compound was a white fluffy solid. Melting point=65° C.–67° C. $^{13}$C NMR(ppm)=119.25.

EXAMPLE 27

Pyrrolidine, 1-[[2-(1-cyclohexen-1-yl)ethyl]amino]acetyl-2-cyano-,(S)-,monohydrochloride

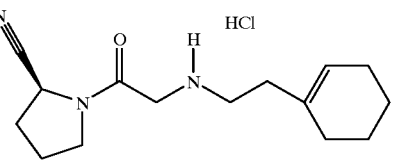

2-(1-Cyclohexenyl) ethylamine (commercially available) was used as the amine nucleophile. The title compound was an off-white fluffy solid. Melting point=162° C.–164° C. $^{13}$C NMR (ppm)=119.27.

EXAMPLE 28

Pyrrolidine, 1-(cyclohexylamino)acetyl-2-cyano-,(S)-,monohydrochloride

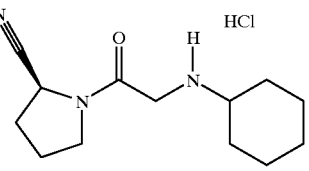

Cyclohexylamine (commercially available) was used as the amine nucleophile. The title compound was a white fluffy solid. Melting point=182° C.–184° C. $^{13}$C NMR (ppm)=119.28.

EXAMPLE 29

Pyrrolidine, 1-[(bicyclo[2.2.1]hept-2-yl)amino]acetyl-2-cyano-[1S[1α,2α(S*),5α]]-(S)-,monohydrochloride

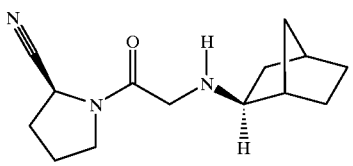

(±)-Exo-2-aminonorbornane (commercially available) was used as the amine nucleophile. The title compound was a white solid. Melting point=98° C.–100° C. $^{13}$C NMR (ppm)=118.36.

EXAMPLE 30

Pyrrolidine, 1-[[2-(2-pyridinyl)ethyl]amino]acetyl-2-cyano-, (S)-,dihydrochloride

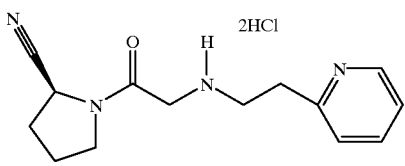

2-(2-Aminoethyl) pyridine (commercially available) was used as the amine nucleophile. The title compound was a white solid. Melting point=95° C.–97° C. $^{13}$C NMR (ppm)= 121.5.

EXAMPLE 31

Pyrrolidine, 1-[[(2-phenylamino)ethyl]amino]acetyl-2-cyano-,(S)-,dihydrochloride

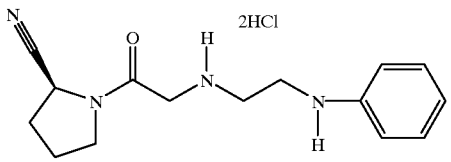

N-phenylethylenediamine (commercially available) was used as the amine nucleophile. The title compound was a white solid. Melting point=124° C.–126° C. $^{13}$C NMR (ppm)=121.4.

EXAMPLE 32

Pyrrolidine, 1-[(3,3-dimethylbutyl)amino]acetyl-2-cyano-,(S)-,monohydrochloride

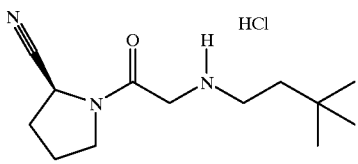

3,3-Dimethylbutylamine (commercially available) was used as the amine nucleophile. The title compound was a white solid. Melting point=164° C.–166° C. $^{13}$C NMR (ppm)=121.5.

EXAMPLE 33

Pyrrolidine,1-[(2,6,6-trimethylbicyclo[3.1.1]hept-3-yl)amino]acetyl-2-cyano-, (S)[1S [1α,2β,3α(S*),5α]]-monohydrochloride

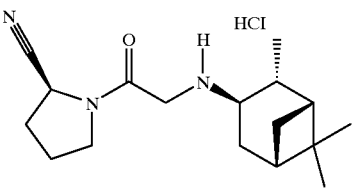

(1R,2R,3R,5S)-(-)-Isopinocampheylamine (commercially available) was used as the amine nucleophile. The title compound was a white solid. Melting point=82° C.—84° C. $^{13}$C NMR (ppm)=121.5.

EXAMPLE 34

Pyrrolidine, 1-[[(1-hydroxymethyl)propyl]amino]acetyl-2-cyano-[S,S)]-

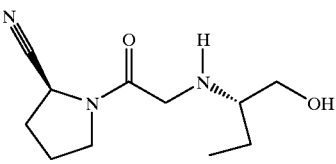

(S)-(+)-2-Amino-1-butanol (commercially available) was used as the amine nucleophile. The title compound was used as an off-white solid. Melting point=80° C.–82° C. $^{13}$C NMR (ppm)=118.2.

EXAMPLE 35

Pyrrolidine, 1-[[[2-[(2-hydroxymethyl)phenyl]thio]phenylmethyl]amino]acetyl-2-cyano-,(S)-,monohydrochloride

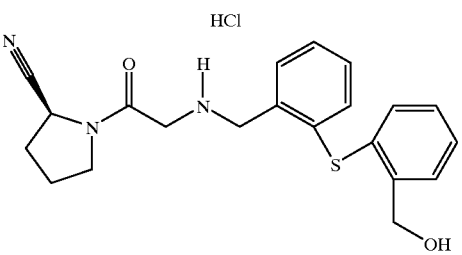

2-(2-(Aminomethyl) phenylthio) benzyl alcohol (commercially available) was used as the amine nucleophile. The title compound was a yellow solid. Melting point=65° C.–67° C. $^{13}$C NMR (ppm)=121.4.

EXAMPLE 36

Pyrrolidine, 1-[[2-(2-methoxyphenyl)ethyl]amino]
acetyl-2-cyano-,(S)-,monohydrochloride

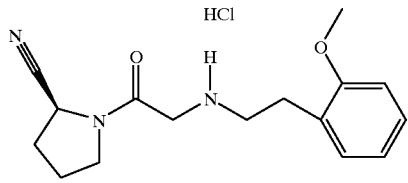

2-Methoxyphenethylamine (commercially available) was used as the amine nucleophile. The title compound was an off white solid. Melting point=174° C. –176° C. $^{13}$C NMR (ppm)=121.7.

EXAMPLE 37

Pyrrolidine, 1-[(5-hydroxypentyl)amino]acetyl-2-cyano-,(S)-,monohydrochloride

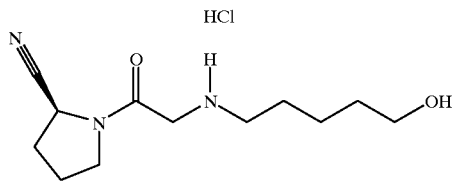

5-Amino-1-pentanol (commercially available) was used as the amine nucleophile. The title compound was a sticky light-green solid. $^{13}$C NME (ppm)=121.67.

EXAMPLE 38

Pyrrolidine, 1-(cyclobutylamino)acetyl-2-cyano-,(S)-monohydrochloride

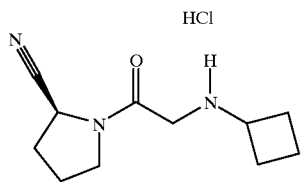

Cyclobutylamine (commercially available) was used as the amine nucleophile. The title compound was an off-white solid. Melting point=274° C.–278° C. decomposed. $^{13}$C NMR (ppm)=121.64.

EXAMPLE 39

Pyrrolidine, 1-[[2-(2,4-dichlorophenyl)ethyl]amino]
acetyl-2-cyano-,(S),monohydrochloride

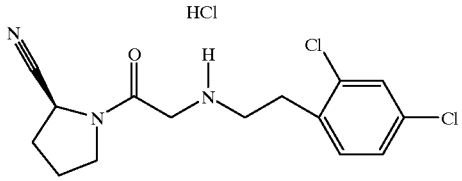

2,4-Dichlorophenethylamine (commercially available) was used as the amine nucleophile. The title compound was a white fluffy solid. Melting point=154° C.–156° C. $^{13}$C NMR (ppm)=121.48.

EXAMPLE 40

Pyrrolidine, 1-[(1-hydroxymethyl]-3-methylbutyl)
amino]acetyl-2-cyano-,O-,(S)-,

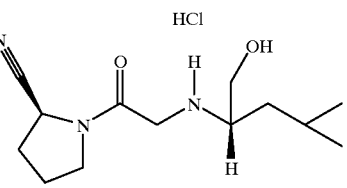

(S)-(+)-Leucinol (commercially available) was used as the amine nucleophile. The title compound was a light yellow solid. Melting point=65° C.–66° C. $^{13}$C NMR (ppm)=117.99.

EXAMPLE 41

Pyrrolidine, 1-[(2-hydroxy-2-phenylethyl)amino]
acetyl-2-cyano-[2S-[1R*,2S*]-monohydrochloride

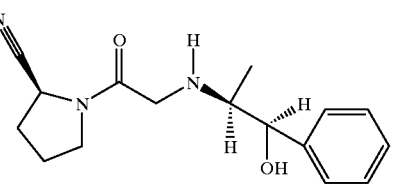

(1R,2S)-(–)-Norephedrine (commercially available) was used as the amine nucleophile. The title compound was a light yellow solid. Melting point=82° C.–83° C. $^{13}$C NMR (ppm)=118.35.

EXAMPLE 42

Pyrrolidine, 1-[[2-(2-fluorophenyl)ethyl]amino]acetyl-2-cyano-,(S)-,monohydrochloride

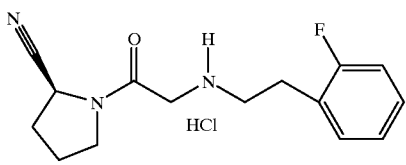

2-Fluorophenethylamine (commercially available) was used as the amine nucleophile. The title compound was a white fluffy solid. Melting point=160° C.–162° C. $^{13}$C NMR (ppm)=121.70.

EXAMPLE 43

Pyrrolidine, 1-(cyclopropylamino)acetyl-2-cyano-,(S)-,monohydrochloride

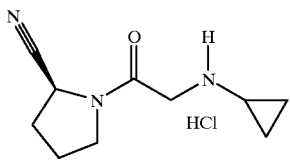

Cyclopropylamine (commercially available) was used as the amine nucleophile. The title compound was an off-white solid. Melting point=170° C.–172° C. $^{13}$C NMR (ppm)=121.62.

EXAMPLE 44

Pyrrolidine, 1-[(2,6,6-trimethylbicyclo[3.1.1]hept-3-yl)amino]acetyl-2-cyano-,[1S[1α,2α,3β(S*),5α]]-monohydrochloride

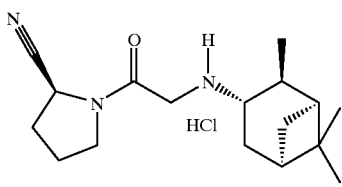

(1S,2S,3S,5R)-(+)-Isopinocampheylamine (commercially available) was used as the amine nucleophile. The title compound was a white solid. Melting point=84° C.–86° C. $^{13}$C NMR (ppm)=121.8.

EXAMPLE 45

Pyrrolidine, 1-[[(2-phenoxy)ethyl]amino]acetyl-2-cyano-,(S)-,monohydrochloride

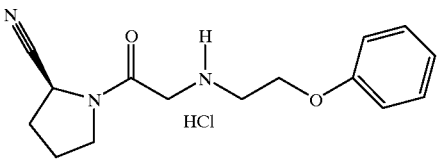

2-Phenoxyethylamine (commercially available) was used as the amine nucleophile. The title compound was a sticky golden solid. $^{13}$C NMR (ppm)=121.7.

EXAMPLE 46

Pyrrolidine, 1-[2-[(3,5-dimethoxyphenyl)ethyl]amino]acetyl-2-cyano-,(S)-,monohydrochloride

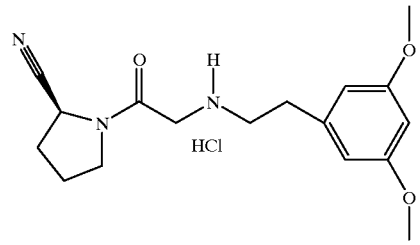

3,5-Dimethoxyphenethylamine (commercially available) was used as the amine nucleophile. The title compound was a white fluffy solid. Melting point=74° C.–76° C. $^{13}$C NMR (ppm)=121.66.

EXAMPLE 47

Pyrrolidine, 1-[(1-adamantyl)amino]acetyl-2-cyano-,(S)-,monohydrochloride

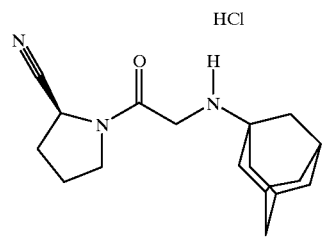

1-Adamantanamine (commercially available) was used as the amine nucleophile. The title compound was a white solid. Melting point=240° C.–242° C. $^{13}$C NMR (ppm)=121.80.

EXAMPLE 48

Pyrrolidine, 1-[(1,1,3,3-tetramethylbutyl)amino]acetyl-2-cyano-,(S)-,monohydrochloride

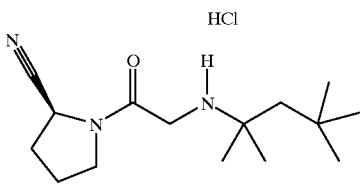

1,1,3,3-Tetramethylbutylamine (commercially available) was used as the amine nucleophile. The title compound was a white fluffy solid. Melting point=68° C.–70° C. $^{13}$C NMR (ppm)=121.55.

EXAMPLE 49

Pyrrolidine, 1-[(2-adamantyl)amino]acetyl-2-cyano-,(S)-,monohydrochloride

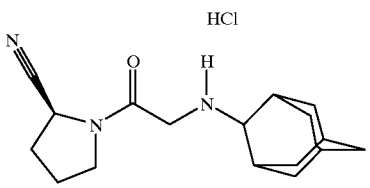

2-Adamantanamine (commercially available) was used as the amine nucleophile. The title compound was an off-white fluffy solid. Melting point=122° C.–124° C. $^{13}$C NMR=(ppm)=121.69.

EXAMPLE 50

Pyrrolidine, 1-[(1,1-dimethylpropyl)amino]acetyl-2-cyano-,(S)-,monohydrochloride

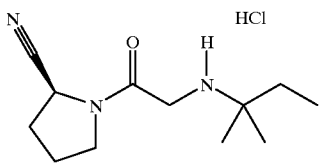

1,1-Dimethylpropylamine (commercially available) was used as the amine nucleophile. The title compound was a white fluffy solid. Melting point=62° C.–64° C. $^{13}$C NMR (ppm)=121.53.

EXAMPLE 51

Pyrrolidine, 1-[(phenylmethyl)amino]acetyl-2-cyano-,(S)-,monohydrochloride

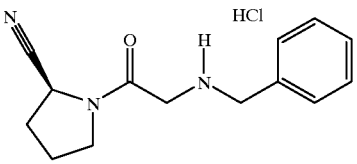

Benzylamine (commercially available) was used as the amine nucleophile. The title compound was a white solid. Melting point=58° C.–60° C. $^{13}$C NMR (ppm)=121.38.

EXAMPLE 52

Pyrrolidine, 1-[(1,1-dimethylethyl)amino]acetyl-2-cyano-,(S),monohydrochloride

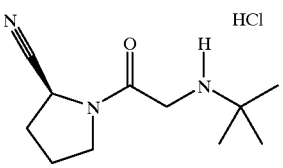

Tert-butylamine (commercially available) was used as the amine nucleophile. The title compound was a white solid. Melting point=226° C.–228° C. $^{13}$C NMR ppm)=121.56.

EXAMPLE 53

Pyrrolidine, 1-[[(2-adamantyl)methyl]amino]acetyl-2-cyano-,(S)-,monohydrochloride

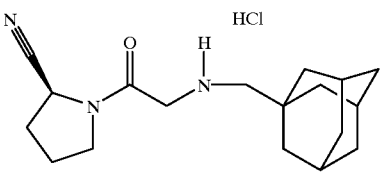

1-Adamnantanemethylamine (commercially available) was used as the amine nucleophile. The title compound was a white solid. Melting point=158° C.–160° C. $^{13}$C NMR=121.56.

EXAMPLE 54

Pyrrolidine, 1-[(2-phenylethyl)amino]acetyl-2-cyano-,(S)-,monohydrochloride

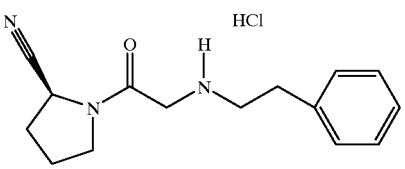

Phenethylamine (commercially available) was used as the amine nucleophile. The title compound was a white solid. Melting point=275° C.–280° C. decomposed. $^{13}$C NMR (ppm)=121.52.

EXAMPLE 55

Pyrrolidine, 1-(pentylamino)acetyl-2-cyano-,(S)-, monohydrochloride

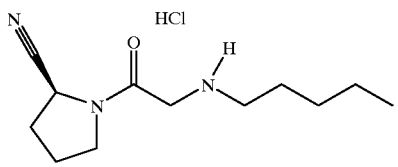

Pentylamine (commercially available) was used as the amine nucleophile. The title compound was a white solid. Melting point 176° C.–178° C. $^{13}$C NMR (ppm)=121.67.

EXAMPLE 56

Pyrrolidine, 1-(butylamino)acetyl-2-cyano-,(S)-, monohydrochloride

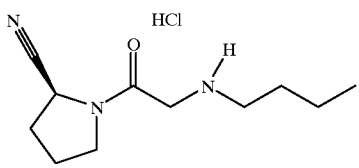

Butylamine (commercially available) was used as the amine nucleophile. The title compound was a white solid. Melting point=180° C.–182° C. $^{13}$C NMR (ppm)=121.56.

EXAMPLE 57

Pyrrolidine, 1-(cyclododecylamino)acetyl-2-cyano-, (S)-,monohydrochloride

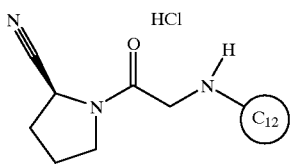

Cyclododecylamine (commercially available) was used as the amine nucleophile. The title compound was a white fluffy solid. $^{13}$C NMR (ppm)=121.52.

EXAMPLE 58

Pyrrolidine, 1-(cyclooctylamino)acetyl-2-cyano-, (S)-,monohydrochloride

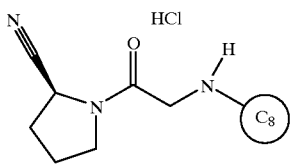

Cyclooctylamine (commercially available) was used as the amine nucleophile. The title compound was a white fluffy solid. $^{13}$C NMR (ppm)=121.64.

EXAMPLE 59

Pyrrolidine, 1-(propylamino)acetyl-2-cyano-,(S)-, monohydrochloride

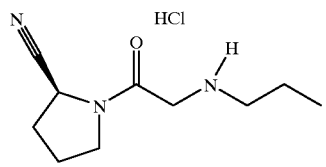

Propylamine (commercially available) was used as the amine nucleophile. The title compound was a white solid. Melting point=193° C.–194° C. $^{13}$C NMR (ppm)=121.57.

EXAMPLE 60

Pyrrolidine, 1-(ethylamino)acetyl-2-cyano-,(S)-, monohydrochloride

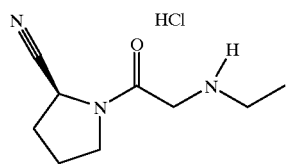

Ethylamine (commercially available) was used as the amine nucleophile. The title compound was an off-white stick solid. $^{13}$C NMR (ppm)=121.67.

EXAMPLE 61

Pyrrolidine, 1-(heptylamino)acetyl-2-cyano-,(S)-, monohydrochloride

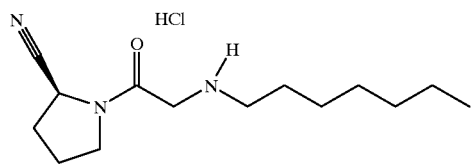

Heptylamine (commercially available) was used as the amine nucleophile. The title compound was a white solid. Melting point=170° C.–172° C. $^{13}$C NMR (ppm)=121.7.

EXAMPLE 62

Pyrrolidine, 1-(hexylamino)acetyl-2-cyano-,(S)-, monohydrochloride

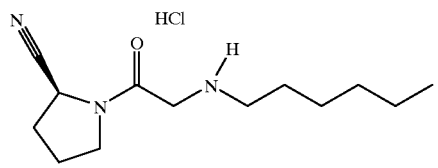

Hexylamine (commercially available) was used as the amine nucleophile. The title compound was a white solid. Melting point=174° C.–176° C. $^{13}$C NMR (ppm)=121.75.

EXAMPLE 63

Pyrrolidine, 1-[[3-[(5-cyano-2-pyridinyl)amino]propyl]amino]acetyl-2-cyano-,(S)-, dihydrochloride

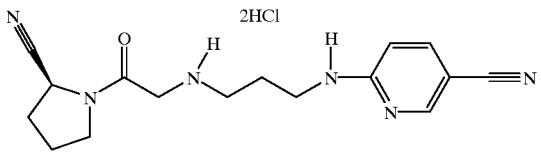

2(3-Aminopropylamino)-5-cyanopyridine (preparation described above) was used as the amine nucleophile. The title compound was a white sticky solid. Melting point=210° C.–212° C. $^{1}$C NMR(pm)=119.33.

EXAMPLE 64

Pyrrolidine, 1-[(1-ethylpropyl)amino]acetyl-2-cyano-,(S)-,monohydrochloride

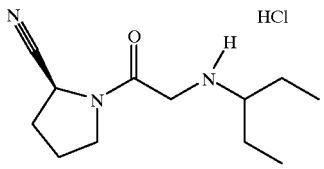

3-Aminopentane (commercially available) was used as the amine nucleophile. The title compound was a white fluffy sticky solid. $^{13}$C NMR ppm)=119.35.

EXAMPLE 65

Pyrrolidine, 1-[(2,3-dihydro-1H-inden-2-yl)amino]acetyl-2-cyano-,(S)-,monohydrochloride

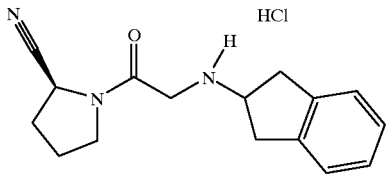

2-Aminoindan (commercially available) was used as the amine nucleophile. The title compound was a white solid. Melting point=182° C.–184° C. $^{13}$C NMR (ppm)=121.38.

EXAMPLE 66

Pyrrolidine, 1-[(1-phenylmethyl-4-piperidinyl)amino]acetyl-2-cyano-,(S)-,-monohydrochloride

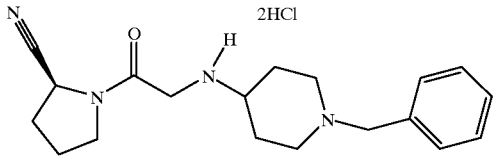

4-Amino-1-benzylpiperidine (commercially available) was used as the amine nucleophile. The title compound was a white solid. Melting point=280° C.–283° C. decomposed. $^{13}$C NMR (ppm)=121.39.

What is claimed is:

1. A compound of formula I:

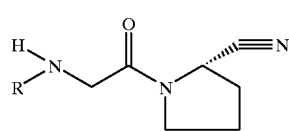

wherein

R is a group $-(CH_2)_m N-R_1$; an unsubstituted $(C_{3-12})$-cycloaklyl ring; a $(C_{3-12})$cycloalkyl ring substituted in the 1-position by a hydroxy($C_{1-3}$)alkyl group; a group $-(CH_2)_n R_2$; a group

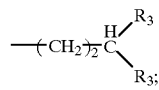

a group $-(CH_2)_p R_4$; an isopropyl group; an isopropyl group substituted in the i-position by a hydroxy($C_{1-3}$)alkyl group; or $R_5$;

$R_1$ is an unsubstituted pyridine ring; a pyridine ring mono- or di-substituted by halo, trifluoromethyl, cyano or nitro; an unsubstituted pyrimidine ring; a pyrimidine ring monosubstituted by halo, trifluoromethyl, cyano or nitro; or an unsubstituted phenyl ring;

$R_2$ is an unsubstituted phenyl ring; a phenyl ring mono-, di- or tri-substituted by halo, ($C_{1-3}$)alkoxy or a phenyl sulfide (optionally substituted with a ($C_{1-8}$)alkoxy); phenoxy; ($C_{1-8}$)alkyl; 3,1,1 bicyclic ring system (optionally substituted with 1 or more ($C_{1-8}$) alkyl groups); unsubstituted pyridine ring; naphthyl, cyclohexene; or adamantyl;

each $R_3$, independently, is an unsubstituted phenyl ring; or a phenyl ring mono-substituted by halo or ($C_{1-3}$) alkoxy;

$R_4$ is a 2-oxopyrrolidine group or a ($C_{2-4}$)alkoxy group;

$R_5$ is indan; pyrrolidine (unsubstituted or substituted with —$CH_2$-phenyl); piperidine (unsubstituted or substituted with —$CH_2$-phenyl); a 2.2,1 bicyclic ring system (unsubstituted or substituted with 1 or more ($C_{1-8}$) alkyl groups); adamantyl; a straight or branched chain ($C_{1-8}$) alkyl (unsubstituted or substituted by one or more substituents selected from hydroxy, —$CH_2OH$ and phenyl); or a 3,1,1 bicyclic ring system (unsubstituted or substituted with 1 or more ($C_{1-8}$)alkyl groups); and m and n independently are integers of 1 to 3;

p is an integer of 2 to 4;

or a pharmaceutically acceptable acid addition salt thereof.

2. A compound according to claim 1 of formula Ia:

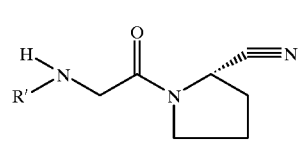

where

R' is a group $-(CH_2)_n N-R_1'$; an unsubstituted ($C_{3-7}$) cycloalkyl ring; a ($C_{3-7}$) cycloalkyl ring substituted in the 1-position by a hydroxy($C_{1-3}$)alkyl group; a group —(CH$_2$)$_3$R$_4$'; or a group R$_5$ as defined in claim 1;

R$_1$' is an unsubstituted pyridine ring; a pyridine ring mono- or di-substituted by halo, trifluoromethyl, cyano or nitro; or an unsubstituted pyrimidine ring; and R$_4$' is a ($C_{2-4}$)alkoxy group;

or a pharmaceutically acceptable acid addition salt thereof.

3. A compound according to claim 2 of formula Ib:

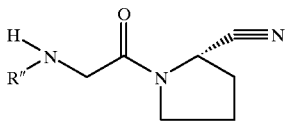

Ib where

R" is a group —(CH$_2$)$_2$N—R$_1$"; a ($C_{4-6}$)cycloalkyl ring substituted in the 1-position by a hydroxy($C_{1-3}$)alkyl group; a group CH$_2$)$_3$R$_4$'; or a group R$_5$';

R$_1$" is a pyridine ring mono- or di-substituted by halo, trifluoromethyl, cyano or nitro;

R$_4$' is as defined in claim 2; and

R$_5$' is a 3,1,1 bicyclic ring system (unsubstituted or substituted with 1 or more ($C_{1-8}$) alkyl groups; a 2,2,1 bicyclic ring system (optionally substituted with 1 or more ($C_{1-8}$) alkyl groups; or adamantyl;

or a pharmaceutically acceptable acid addition salt thereof.

4. A compound according to claim 3 of formula Ic:

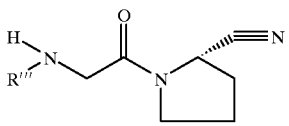

Ic where

R'" is a group —(CH$_2$)$_2$N—R$_1$'"; a ($C_{4-6}$)cycloalkly ring substituted in the 1-position by a hydroxymethyl group; a group —(CH$_2$)$_3$R$_4$"; or a group R$_5$";

R$_1$'" is a pyridine ring monosubstituted by halo, trifluoromethyl, cyano or nitro;

R$_4$' is as defined in claim 3; and

R$_5$&41 is adamantyl;

or a pharmaceutically acceptable acid addition salt thereof.

5. A compound of formula I:

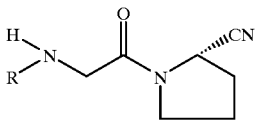

I wherein R is:

a) R$_1$R$_{1a}$N(CH$_2$)$_m$- wherein

R$_1$ is a pyridinyl or pyrimidinyl moiety unsubstituted or mono- or independently disubstituted with ($C_{1-4}$) alkyl, ($C_{1-4}$)alkoxy, halogen, trifluoromethyl, cyano or nitro; or phenyl unsubstituted or- or independently disubstituted with ($C_{1-4}$)alkyl, ($C_{1-4}$)alkoxy or halogen;

R$_{2a}$ is hydrogen or ($C_{1-8}$alkyl; and m is 2 or3;

b) ($C_{3-12}$)cycloalkyl unsubstituted or monosubstituted in the 1-position with ($C_{1-3}$)hydroxyalkyl;

c) R$_2$(CH$_2$)$_n$- wherein either

R$_2$ is phenyl unsubstituted or mono- or independently di- or independently trisubstituted with ($C_{1-4}$)alkyl, ($C_{1-4}$)alkoxy, halogen or phenylthio unsubstituted or monosubstituted in the phenyl ring with hydroxymethyl; or is ($C_{1-8}$)alkyl; a [3.1.1]bicyclic carbocyclic moiety unsubstituted or mono- or plurisubstituted with ($C_{1-8}$)alkyl; a pyridinyl or naphthyl moiety unsubstituted or mono- or independently disubstituted with ($C_{1-4}$)alkyl, ($C_{1-4}$)alkoxy or halogen; cyclohexene; or adamantyl; and n is 1 to 3; or R$_2$ is phenoxy unsubstituted or mono- or independently disubstituted with ($C_{1-4}$), ($C_{1-4}$)alkoxy or halogen; and n is 2or3;

d) (R$_3$)$_2$CH(CH$_2$)$_2$- wherein each R$_3$ independently is phenyl unsubstituted or mono- or independently disubstituted with ($C_{1-4}$)alkyl, ($C_{1-4}$)alkoxy or halogen;

e) R$_4$(CH$_2$)$_p$- wherein R$_4$ is 2-oxopyrrolidinyl or ($C_{2-4}$) alkoxy and p is2to4;

f) isopropyl unsubstituted or monosubstituted in the 1 -position with ($C_{1-3}$)hydroxyalkyl;

g) R$_5$ wherein R$_5$ is: indanyl; a pyrrolidinyl or piperidinyl moiety unsubstituted or substituted with benzyl; a [2.2.1]- or [3.1.1]bicyclic carbocyclic moiety unsubstituted or mono- or plurisubstituted with ($C_{1-8}$)alkyl; adamantyl; or ($C_{1-8}$)alkyl unsubstituted or mono- or independently plurisubstituted with hydroxy, hydroxymethyl or phenyl unsubstituted or mono- or independently disubstituted with ($C_{1-4}$)alkyl, ($C_{1-4}$) alkoxy or halogen;

in free form or in acid addition salt form.

6. A compound according to claim 5 (a compound Ip) wherein R is R$^p$, which is:

a) R$_1^p$NH(CH$_2$)$_2$- wherein R$_1^p$ is a pyridinyl or pyrimidinyl moiety unsubstituted or mono- or independently disubstituted with halogen, trifluoromethyl, cyano or nitro;

b) ($C_{3-7}$)cycloalkyl unsubstituted or the monosubstituted in 1-position with ($C_{1-3}$)hydroxyalkyl;

c) R$_2^p$(CH$_2$)$_2$- wherein R$_2^p$ is phenyl unsubstituted or mono- or independently di- or independently trisubstituted with halogen or ($C_{1-3}$)alkoxy;

d) (R$_3^p$)$_2$CH(CH$_2$)$_2$- wherein each R$_3^p$ independently is phenyl substituted or monosubstituted with halogen or ($C_{1-3}$)alkoxy;

e) R$_4$(CH$_2$)$_3$- wherein R$_4$ is as defined in claim 5; or f) isopropyl unsubstituted or monosubstituted in 1-position with ($C_{1-3}$)hydroxyalkyl;

in free form or in acid addition salt form.

7. A compound according to claim 5 (a compound Is), wherein R is R$^s$, which is:

a) R$_1^s$R$_{1a}^s$(CH$_2$)$_{ms}$- wherein R$_1^s$ is pyridinyl unsubstituted or mono- or independently disubstituted with chlorine, trifluoromethyl, cyano or nitro; pyrimidinyl unsubstituted or monosubstituted with chlorine or trifluoromethyl; or phenyl; R$_{1a}^s$ is hydrogen or methyl; and ms is2or3;

b) ($C_{3-12}$)cycloalkyl unsubstituted or monosubstituted in the 1-position with hydroxymethyl;

c) R$_2^s$(CH$_2$)$_{ns}$- wherein either R$_2^s$ is phenyl unsubstituted or mono- or independently di- or independently trisubstituted with halogen, alkoxy of 1 or 2 carbon atoms or phenylthio monosubstituted in the phenyl ring with hydroxymethyl; $(C_{1-6})$alkyl; 6,6-dimethylbicyclo[3.1.1]hept-2-yl; pyridinyl; naphthyl; cyclohexene; or adamantyl; and ns is 1 to 3; or $R_2^s$ is phenoxy; and ns is 2;

d) (3,3-diphenyl)propyl;

e) $R_4^s(CH_2)_{ps}$ wherein $R_4^s$ is 2-oxopyrrolidin-1-yl or isopropoxy and ps is 2 or 3;

f) isopropyl unsubstituted or monosubstituted in 1-position with hydroxymethyl;

g) $R_5^s$ wherein $R_5^s$ is: indanyl; a pyrrolidinyl or piperidinyl moiety unsubstituted or N-substituted with benzyl; bicyclo[2.2.1]hept-2-yl; 2,6,6-trimethylbicyclo-[3.1.1]hept-3-yl; adamantyl; or $(C_{1-8})$alkyl optionally mono- or independently disubstituted with hydroxy, hydroxymethyl or phenyl;

in free form or in acid addition salt form.

8. The compound according to claim 5 wherein R is 2-[(5-cyanopyridin-2-yl)amino]ethyl, i.e. 1-[2-[(5-cyanopyridin-2-yl)amino]ethylamino]acetyl-2-cyano-(S)-pyrrolidine, in free form or in acid addition salt form, or a compound according to claim 5 which is of formula I wherein R is either 2-[(5-chloropyridin-2-yl)amino]ethyl, or
(1-hydroxymethyl)cyclopent-1-yl, or
2-[(5-nitropyridin-2-yl)amino]ethyl, or
3-(isopropoxy)propyl, in free form or in acid addition salt form.

9. A compound according to claim 5 which is:

1-[2-[(5-chloropyridin-2-yl)amino]ethylamino]acetyl-2-cyano-(S)-pyrrolidine dihydrochloride;
1-[2-[(5-trifluoromethylpryridin-2-yl)amino]ethylamino]acetyl-2-cyano-(S)-pyrrolidine;
1-[2-[(5-cyanopyridin-2-yl)amino]ethylamino]acetyl-2-cyano-(S)-pyrrolidine dihydrochloride;
1-[2-[(pyrimidin-2-yl)amino]ethylamino]acetyl-2-cyano-(S)-pyrrolidine;
1-[(1-hydroxymethylcyclopent-1-yl)amino]acetyl-2-cyano-(S)-pyrrolidine;
1-[2-[(pyridin-2-yl)amino]ethylamino]acetyl-2-cyano-(S)-pyrrolidine;
1-[2-[(4-chloropyrimidin-2-yl)amino]ethylamino]acetyl-2-cyano-(S)-pyrrolidine;
1-[2-[(3-chloropyridin-2-yl)amino]ethylamino]acetyl-2-cyano-(S)-pyrrolidine;
1-[2-[4-trifluoromethylpyrimidin-2-yl)amino]ethylamino]acetyl-2-cyano-(S)-pyrrolidine;
1-[(2-chlorophenyl)ethylamino]acetyl-2-cyano-(S)-pyrrolidine;
1-[(3,3-diphenyl)propylamino]acetyl-2-cyano-(S)-pyrrolidine;
1-[2-[(5-nitropyridin-2-yl)amino]ethylamino]acetyl-2-cyano-(S)pyrrolidine;
1-[2-[(3-chloro-5-trifluoromethylpyridin-2-yl)amino]ethylamino]acetyl-2-cyano-(S)-pyrrolidine;
1-[2-[(3-trifluoromethylpyridin-2-yl)amino]ethylamino]acetyl-2-cyano-(S)pyrrolidine;
1-[2-[(3,5-dichloropyridin-2-yl)amino]ethylamino]acetyl-2-cyano-(S)-pyrrolidine;
1-[(cyclopent-1-yl)amino-acetyl-2-cyano-(S)-pyrrolidine monohydrochloride;
1-[2-(2-bromo-4,5-dimethoxyphenyl)ethylamino]acetyl-2-cyano-(S)-pyrrolidine;
1-[3-(isopropoxy)propylamino]acetyl-2-cyano-(S)-pyrrolidine monohydrochloride;
1-[(2-hydroxy-1,1-dimethylethylamino)]acetyl-2-cyano-(S)-pyrrolidine monohydrochloride;
1-[3-(2-oxo-pyrrolidin-1-yl)propylamino]acetyl-2-cyano-(S)-pyrrolidine monohydrochloride;
1-[(1-hydroxymethylcylohexyl)amino]acetyl-2-cyano-(S)-pyrrolidine;
Pyrrolidine, 1-[[2-(4-ethoxyphenyl)ethyl]amino]acetyl-2-cyano-,(S)-,monohydrochloride;
Pyrrolidine, 1-[(1-phenylmethyl-3-pyrrolidinyl)amino]acetyl-2-cyano-,(S)-(R)-,dihydrochloride;
Pyrrolidine, 1-[[2-(4-methoxyphenyl)ethyl]amino]acetyl-2-cyano-,(S)-,monohydrochloride;
Pyrrolidine, 3-[[2-(3-methoxyphenyl)ethyl]amino]acetyl-2-cyano-,(S)-,monohydrochloride;
Pyrrolidine, 1-[[(1-naphthalenyl)methyl]amino]acetyl-2-cyano-,(S)-,monohydrochloride;
Pyrrolidine, 1-[(3-phenylpropyl)amino]acetyl-2-cyano-,(S)-,monohydrochloride;
Pyrrolidine, 1-[[3-[(phenyl)(methyl)amino]propyl]amino]acetyl-2-cyano-,(S)-,dihydrochloride;
Pyrrolidine, 1-[2-[(3,4-dimethoxyphenyl)ethyl]amino]acetyl-2-cyano-,(S)-,monohydrochloride;
Pyrrolidine, 1-(acycloheptylamino)acetyl-2-cyano-,(S)-, monohydrochloride;
Pyrrolidine, 1-[[(6,6-dimethylbicyclo[3.1.1]hept-2-yl)methyl]amino]acetyl-2-cyano-[1S[1α,2α(S*),5α]]-(S)-, monohydrochloride;
Pyrrolidine, 1-[[2-(2,5-dmethoxyphenyl)ethyl]amino]acetyl-2-cyano-,(S)-,monohydrochloride;
Pyrrolidine, 1-[[2-(1-cyclohexen-1-yl)ethyl]amino]acetyl-2-cyano-,(S)-;
Pyrrolidine, 1-(cyclohexylamino)acetyl-2-cyano-,(S)-, monohydrochloride;
Pyrrolidine, 1-[(bicyclo[2.2.1]hept-2-yl)amino]acetyl-2-cyano-[1S[1α,2α(S*),5α]]-(S)-,monohydrochloride;
Pyrrolidine, 1-[[2-(2-pyridinyl)ethyl]amino]acetyl-2-cyano-,(S)-,dihydrochloride;
Pyrrolidine, 1-[[(2-phenylamino)ethyl]amino]acetyl-2-cyano-,(S)-,dihydrochloride;
Pyrrolidine, 1-[(3,3-dimethylbutyl)amino]acetyl-2-cyano-,(S)-,monohydrochloride;
Pyrrolidine, 1-[(2,6,6-trimethylbicyclo[3.1.1]hept-3-yl)amino]acetyl-2-cyano-,(S)[1S[1α,2β,3α(S*),5α]]-monohydrochloride;
Pyrrolidine, 1-[[(1-hydroxymethyl)propyl]amino]acetyl-2-cyano-[S,S)]-;
Pyrrolidine, 1-[[[2-[(2-hydroxymethyl)phenyl]thio]phenylmethyl]amino]acetyl-2-cyano-,(S)-, monohydrochloride;
Pyrrolidine, 1-[[2-(2-methoxyphenyl)ethyl]amino]acetyl-2-cyano-,(S)-,monohydrochloride;
Pyrrolidine, 1-[(5-hydroxypentyl)amino]acetyl-2-cyano-,(S)-,monohydrochloride;
Pyrrolidine, 1-(cyclobutylamino)acetyl-2-cyano-,(S)-monohydrochloride;
Pyrrolidine, 1-[[2-(2,4dichlorophenyl)ethyl]amino]acetyl-2-cyano-,(S),monohydrochloride;
Pyrrolidine, 1-[(1-hydroxymethyl]-3-methylbutyl)amino]acetyl-2-cyano-,O-,(S)-,;
Pyrrolidine, 1-[(2-hydroxy-2-phenylethyl)amino]acetyl-2-cyano-[2S-[1R*,2S*]-monohydrochloride;
Pyrrolidine, 1-[[2-(2-fluorophenyl)ethyl]amino]acetyl-2-cyano-,(S)-,monohydrochloride;
Pyrrolidine, 1-(cyclopropylamino)acetyl-2-cyano-,(S)-, monohydrochloride;
Pyrrolidine, 1-[(2,6,6-trimethylbicyclo[3.1.1]hept-3-yl)amino]acetyl-2-cyano-[1S[1α,2α,3β(S*),5α]]-monohydrochloride;
Pyrrolidine, 1-[[(2-phenoxy)ethyl]amino]acetyl-2-cyano-,(S)-,monohydrochloride;

Pyrrolidine, 1-[2-[(3,5-dimethoxyphenyl)ethyl]amino]acetyl-2-cyano-,(S)-,monohydrochloride;
Pyrrolidine, 1-[(1-adamantyl)amino]acetyl-2-cyano-,(S)-, monohydrochloride;
Pyrrolidine, 1-[(1,1,3,3-tetramethylbutyl)amino]acetyl-2-cyano-,(S)-,monohydrochloride;
Pyrrolidine, 1-[(2-adamantyl)amino]acetyl-2-cyano-,(S)-, monohydrochloride;
Pyrrolidine, 1-[(1,1-dimethylpropyl)amino]acetyl-2-cyano-, (S)-,monohydrochloride;
Pyrrolidine, 1-[(phenylmethyl)amino]acetyl-2-cyano-,(S)-, monohydrochloride;
Pyrrolidine, 1-[(1,1-dimethylethyl)amino]acetyl-2-cyano-, (S),monohydrochloride;
Pyrrolidine, 1-[[(2-adamantyl)methyl]amino]acetyl-2-cyano-,(S)-,monohydrochloride;
Pyrrolidine, 1-[(2-phenylethyl)amino]acetyl-2-cyano-, (S)-, monohydrochloride;
Pyrrolidine, 1-(pentylamino)acetyl-2-cyano-,(S)-, monohydrochloride;
Pyrrolidine, 1-(butylamino)acetyl-2-cyano-,(S)-, monohydrochloride;
Pyrrolidine, 1-(cyclododecylamino)acetyl-2-cyano-,(S)-, monohydrochloride;
Pyrrolidine, 1-(cyclooctylamino)acetyl-2-cyano-,(S)-, monohydrochloride;
Pyrrolidine, 1-(propylamino)acetyl-2-cyano-,(S)-, monohydrochloride;
Pyrrolidine, 1-(ethylamino)acetyl-2-cyano-,(S)-, monohydrochloride;
Pyrrolidine, 1-(heptylamino)acetyl-2-cyano-,(S)-, monohydrochloride;
Pyrrolidine, 1-(hexylamino)acetyl-2-cyano-,(S)-, monohydrochloride;
Pyrrolidine, 1-[[3-[(5-cyano-2-pyridinyl)amino]propyl]amino]acetyl-2-cyano-,(S)-,dihydrochloride;
Pyrrolidine, 1-[(1-ethylpropyl)amino]acetyl-2-cyano-,(S)-, monohydrochloride,
Pyrrolidine, 1-1(2,3-dihydro-1H-inden-2-yl)amino]acetyl-2-cyano-,(S)-,monohydrochloride;
Pyrrolidine, 1-[(1-phenylmethyl-4-piperidinyl)amino]acetyl-2-cyano-,(S)-,
monohydrochloride; or a pharmaceutically acceptable salt of any of the above compounds which are in free form.

10. A pharmaceutical composition comprising a compound according to claim 5 in free form or in pharmaceutically acceptable acid addition salt form, together with at least one pharmaceutically acceptable carrier or diluent.

11. A compound according to claim 8 which is 1-[2-[(5cyanopyridin-2-yl)amino]ethylamino]acetyl-2-cyano-(S)-pyrrolidine dihydrochloride.

* * * * *